(12) United States Patent
Sun

(10) Patent No.: US 10,314,995 B2
(45) Date of Patent: Jun. 11, 2019

(54) ENDOTRACHEAL INTUBATION AND SUPRAGLOTTIC AIRWAY DEVICE

(71) Applicant: Yang Sun, San Francisco, CA (US)

(72) Inventor: Yang Sun, San Francisco, CA (US)

(*) Notice: Subject to any disclaimer, the term of this patent is extended or adjusted under 35 U.S.C. 154(b) by 0 days.

(21) Appl. No.: 15/679,164

(22) Filed: Aug. 17, 2017

(65) Prior Publication Data
US 2019/0054266 A1 Feb. 21, 2019

(51) Int. Cl.
| A61M 16/04 | (2006.01) |
| A61B 1/267 | (2006.01) |
| A61B 1/07 | (2006.01) |
| A61B 1/00 | (2006.01) |

(52) U.S. Cl.
CPC ..... *A61M 16/0488* (2013.01); *A61B 1/00135* (2013.01); *A61B 1/00142* (2013.01); *A61B 1/07* (2013.01); *A61B 1/267* (2013.01); *A61M 16/044* (2013.01); *A61M 16/0409* (2014.02); *A61M 16/0411* (2014.02); *A61M 16/0418* (2014.02); *A61M 16/0431* (2014.02); *A61M 16/0447* (2014.02); *A61M 16/0463* (2013.01); *A61M 16/0486* (2014.02)

(58) Field of Classification Search
CPC .......... A61M 16/0409; A61M 16/0411; A61M 16/0418; A61M 16/0434; A61M 16/0463; A61M 16/0486; A61M 16/0488; A61M 16/044
See application file for complete search history.

(56) References Cited

U.S. PATENT DOCUMENTS

| 4,067,331 A | 1/1978 | Berman |
| 4,329,983 A | 5/1982 | Fletcher |
| 5,303,697 A | 4/1994 | Brain |
| 5,392,774 A | 2/1995 | Sato |
| 5,632,271 A | 5/1997 | Brain |
| 6,672,305 B2 | 1/2004 | Parker |
| 6,698,430 B2 | 2/2004 | Van Landuyt |
| 6,729,325 B2 | 5/2004 | Alfery |
| 6,792,948 B2 | 9/2004 | Brain |
| 6,901,928 B2 | 6/2005 | Loubser |
| 7,040,312 B2 | 5/2006 | Alfery |
| 7,174,889 B2 | 2/2007 | Boedeker |
| RE39,508 E | 5/2007 | Parker |
| 7,500,948 B2 | 5/2009 | Cantrell |
| 7,506,648 B2 | 5/2009 | Brain |
| 7,878,201 B2 | 2/2011 | Mongeon |
| 7,896,007 B2 | 3/2011 | Brain |

(Continued)

*Primary Examiner* — Valerie L Woodward
(74) *Attorney, Agent, or Firm* — David Olsen; Olsen Patent Law

(57) ABSTRACT

An intubation and supraglottic airway medical device. The device includes an air tube for ventilation, and a tube for guiding a fiber-optic-probe-scope to the distal end of the device. The distal end of the device is configured with a balloon around the tube system and between a bottom plate and the tube system such that when inflated the distal end of the air-tube is moved and thereby positioning the air-tube distal opening in front of a laryngeal inlet. Additionally, the balloon forms a seal with the surrounding tissue. The device includes a drainage loop and an esophageal blocker preventing aspiration. The air tube distal end can include a lifting plate configured to lift an epiglottis when the balloon is inflated.

27 Claims, 14 Drawing Sheets

(56) References Cited

U.S. PATENT DOCUMENTS

| | | |
|---|---|---|
| 7,997,274 B2 | 8/2011 | Baska |
| 8,166,967 B2 | 5/2012 | Qiu |
| 8,220,454 B2 | 7/2012 | Murray |
| 8,419,634 B2 | 4/2013 | Nearman |
| 8,449,713 B2 | 5/2013 | Brain |
| 8,522,789 B2 | 9/2013 | Miller |
| D693,920 S | 11/2013 | Miller |
| 8,631,796 B2 | 1/2014 | Cook |
| 8,777,848 B2 | 7/2014 | Dhonneur |
| D769,442 S | 10/2016 | Nasir |
| 9,498,591 B2 | 11/2016 | Brain |
| 9,675,772 B2 | 6/2017 | Brain |
| 9,694,150 B2 | 7/2017 | Brain |
| 2002/0189618 A1* | 12/2002 | Augustine .............. A61B 1/267 128/207.15 |
| 2003/0041862 A1 | 5/2003 | Imai |
| 2008/0029100 A1 | 2/2008 | Glassenberg |
| 2008/0115783 A1* | 5/2008 | Brain ................... A61M 16/04 128/200.26 |
| 2011/0023890 A1* | 2/2011 | Baska ................... A61M 16/04 128/207.15 |
| 2013/0269689 A1* | 10/2013 | Brain ................... A61M 16/04 128/200.26 |
| 2014/0309494 A1* | 10/2014 | Molnar ................. A61B 7/003 600/109 |
| 2014/0333007 A1 | 11/2014 | Nasir |
| 2016/0206841 A1* | 7/2016 | Vadivelu ........... A61M 16/0463 |

* cited by examiner

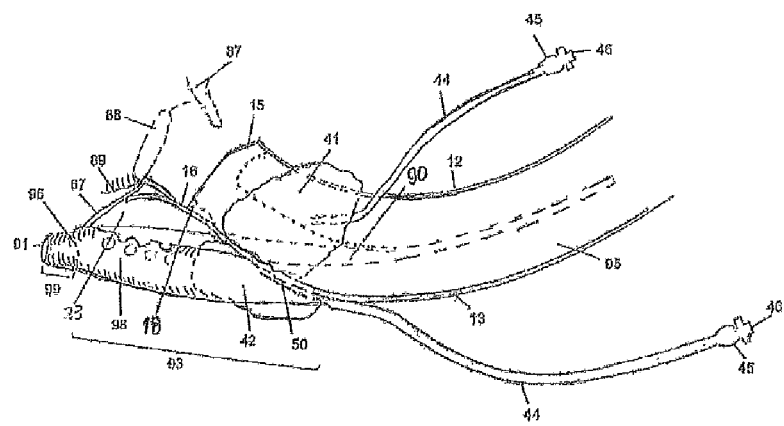

Fig.10
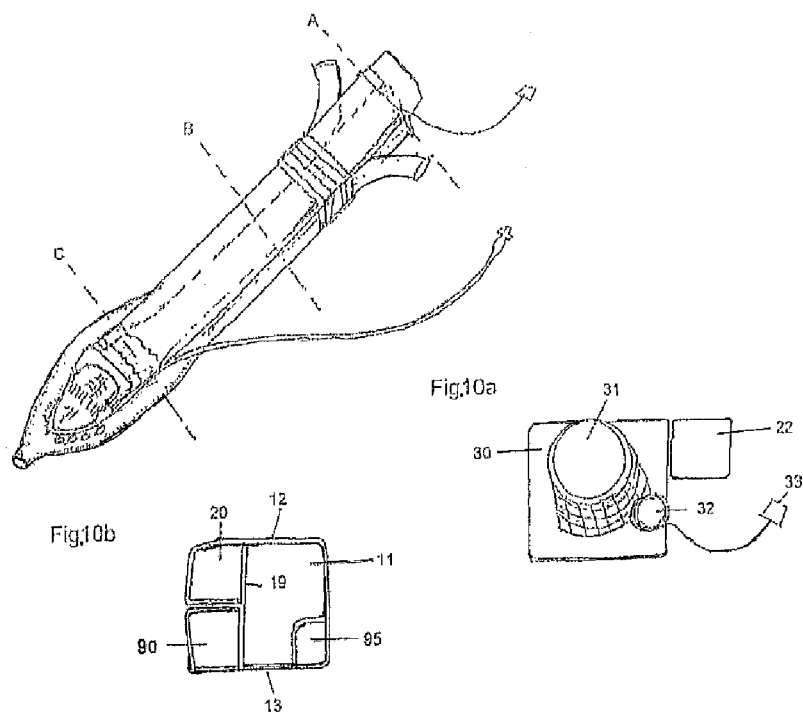
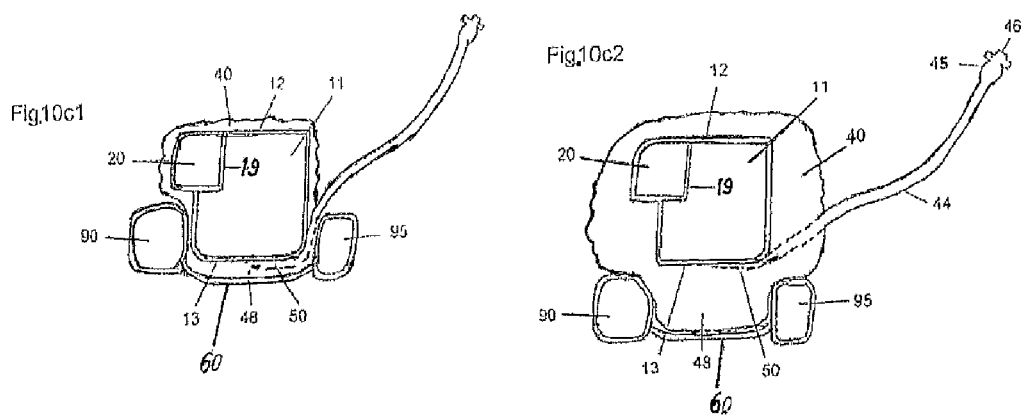

ENDOTRACHEAL INTUBATION AND SUPRAGLOTTIC AIRWAY DEVICE

CROSS REFERENCE TO OTHER APPLICATIONS

Field of Invention

The present invention relates to medical airway management devices and methods for easily and gently intubating a patient or animal, with a choice of "blind" intubating or under vision of a built-in channel capable for a fiber optic scope in people and animals, and without requiring a patient's specific head position. The present invention is designed to provide multiple functions for use in routine and difficulty airway in operating room, intensive care units, emergency rooms, in-hospital and pre-hospital resuscitation, and off campus surgical center.

The invention also relates to devices that can serve as an independent supraglottic airway device for spontaneous and positive pressure mechanical ventilation where intubation is not desired. Further, the invention relates to devices that provide access to the larynx inlet, vocal cords and tracheal for diagnosis and treatment.

BACKGROUND

Intubation:

For decades, a daily used traditional metal blade laryngoscope was commonly employed to place an endotracheal tube into a person's trachea. However, a blade laryngoscope presents significant patient risks. These risks include dental injury, airway tissue injury, and further injury to patient's with a neck injury caused by neck manipulation during intubation. A further limitation is the limited ability or inability to visualize vocal cord for intubation, if a full dose of a muscle relaxant was not given to increase the opening a patient's mouth for insertion of a metal laryngoscope blade. The muscle relaxant can have additional detrimental side effects. Multiple attempts of intubation by a traditional metal laryngoscope also significantly increase the risk of morbidity and mortality.

The many prior art devices have been used in a routine or difficult endotracheal intubation cases. They can be divided roughly into four categories: traditional and video laryngoscopy, supraglottic airway device, fiber optic scope intubation and others.

In the first category, the traditional Miller and Macintosh metal laryngoscopy which has been used for many decades. Currently, there are many video laryngoscopes in clinical use, such as the Glidescope, McGrath, Airtraq, C-Mac, Berci-Kaplan DCI, Pentax Airway Scope, Truview EVO, and APA video laryngoscopy. These video laryngoscopy devices rely on obtaining an indirect view of the epiglottis and glottis inlet during intubation. However, their basic blade design is based on a traditional Macintosh metal blade plus a visualization capability that can incorporate a viewing screen. Their blade's shape and curve are rigid and very similar to traditional Macintosh metal laryngoscopy blade in shape and curvature. They carry the same disadvantage of the traditional metal blade. Their hard rigid preformed prominent curve makes them difficulty to insert and can easily cause damage to a patient's airway. Therefor their use require a full dose of a muscle relaxant medication to open the patient's mouth wide. A variety of types of trauma, airway bleeding, heavy secretion, or a patient's injury requires intubation in an unusual position, such as in a car wreck or with a cervical spine injury which is better to be intubated without moving their head or body position, all those clinical situation can make direct or indirect visual observation of the vocal cords very difficult if not impossible by traditional metal laryngoscopes or by video laryngoscopes. Another disadvantage of video laryngoscopes is that they are expensive to manufacture.

The second category includes supraglottic airway devices including different types of laryngeal mask airway, brief as LMA, I-gel, intubation laryngeal mask airway, air-Qsp, laryngeal tube and others. These devices are mainly made of plastic materials and designed as a supraglottic airway for a patient's ventilation in routine and emergency cases. One drawback of this type device is that the tip of LMA can fold during insertion or can be compressed and twisted by surrounding tissues to block ventilation. And the cuff can exert excessive pressure to the tissues in one area and have not enough sealing pressure in another area causing the air leaking and possibility of aspiration of esophageal gastric content. In a newly designed LMA supreme, the rigid pre-formed curve can cause tissue damage and the pre-formed curve and fixed length from the curve to the distal end makes it very difficult for the device to fit the varying anatomy of each patient. These problems can be greatly exaggerated in mechanical ventilation scenarios, especially in an obese patient.

The second device category claims the capability of placement of an endotracheal tube through the device. Intubation laryngeal mask airway, brief as ILMA, was especially designed for blind intubation without visualization of the laryngeal inlet or vocal cords. However, the ILMA has a metal handle with a very prominent curved region making it difficult to insert into a patient's mouth. Second, the ILMA relies on precisely positioning and alignment of the epiglottis with the recessed epiglottis elevation bar. This precise position is required so that the epiglottis elevation bar can raise the epiglottis out of the way of an advancing endotracheal tube. Such precise position is often hard to achieve. Otherwise the operator has to rock the device back and forth to try to achieve the correct alignment. This device movement can cause a lot of damage to a patient's airway tissues. Further, the endotracheal tube can become lodged against the edge of laryngeal inlet or vocal cords due to the angle of the endotracheal tube entering the glottis opening. So ILMA requires a specially made and expensive endotracheal tube. Often times this tube needs to be changed to a regular endotracheal tube if the patient needs mechanical ventilation after surgery. In addition, ILMA still has the same problems as other types of LMA due to their basic design concepts. In one prior art, U.S. Pat. No. 8,128,071, optical fibers were added to gain visualization of the laryngeal anatomy, but this device still suffers from the limitations stated above.

For the third category of devices, the use of a flexible fiber-optic scope intubation of the trachea has been used in medical practice for decades which allows for placement of an endotracheal tube with minimal manipulation of the patients airway. While this technique had been considered the gold standard in cases with awake patient intubation, this technique is time consuming and not suitable in emergency situations and the use of this type of device requires significant skill and training The fourth type of prior art devices incorporates guides for intubation. U.S. Pat. No. 4,832,020, "Tracheal Intubation Guide," U.S. Pat. No. 6,672,305 in 1989, "Shallow Throat Orotracheal Intubation Guide" and RE39,508 E, 2007 "Blind Orolaryngeal and Oroesophageal Guiding Aiming Device" disclose a tracheal intubation guide which sits above the glottis. However, such a design does not assurance stable alignment of the device with respect to the laryngeal opening. Therefore, an endotracheal tube can be misguided and cause miss-intubation and laryngeal trauma. In another prior art, U.S. Pat. No. 7,040,312, 2006, "Peri-laryngeal Oral Airway" it discloses an oral airway that can be used to guide an endotracheal tube into a trachea by axially advancing the endotracheal tube through a gap defined by the material forming the grate of the wedge-shaped housing. But this depends on where the wedge shaped housing is inserted. Therefore, intended result is very difficult to be achieved.

Positive Pressure Mechanical Ventilation:

It is standard practice of requiring endotracheal intubation on a patent when positive mechanical ventilation is planned. Using a supraglottic airway device for spontaneous ventilation has been widely accepted, but not for mechanical ventilation. All currently used supraglottic airway devices can result significantly air leaking out patient's mouth during positive pressure mechanic ventilation even when an associated balloon is inflated to a high pressure which can cause damage to the airway tissues, and air insufflation into patient's stomach. And in comparison to traditional endotracheal tube, various supraglottic airway devices need a higher inspiration pressure to achieve the same tidal volume of ventilation. However, the higher inspiration pressure can cause gastric contents regurgitation and pulmonary aspiration and at same time the higher inspiration pressure is hard to achieve due to air leakage.

The objectives of the various embodiments of this invention are to minimize and mitigate the complication, co-morbidity, and to achieve more effective intubation and ventilation.

Glossary of Acronyoms and Abbreviations

ATAP—Air tube alignment plate
ISAD—Intubation and Supraglottic Airway Device.
LMA—Laryngeal Mask Airway
ELHP—Epiglottis lifting and holding plate

BRIEF DESCRIPTION OF THE DRAWINGS

FIG. 9a—Close up left side view of two independent balloons configuration in an alternative embodiment with two separated inflation tubes, both balloons inflated, the pressure buffering chamber and the gas exchange chamber created, the balloon located under the bottom wall of the tube system distal segment compressing the under-balloon segment to near closed status.

FIG. 9b1—Side view of an inflatable balloon incompletely encircling a length of the tube system distal segment form below in an alternative embodiment, the inflated balloon compressing the under-balloon segment to near closed status.

FIG. 9b2—Cross section view from distal side of FIG. 9b1, with cross section view of the bottom plate added into the drawing.

FIG. 10—Multiple cross-sectional view lines of the ISAD.

FIG. 10a—Cross section view of the connection interface from proximal side.

FIG. 10b—Cross section view of the tube system middle segment from the distal side.

FIG. 10c1—Cross section view of the air tube distal end from distal side with the balloon deflated, the under-balloon segment not being compressed.

FIG. 10c2—Cross section view of FIG. 10c1 with the balloon inflated, the inflated balloon compressing the under-balloon segment to near closed status.

SUMMARY OF INVENTION

Figure 1A:
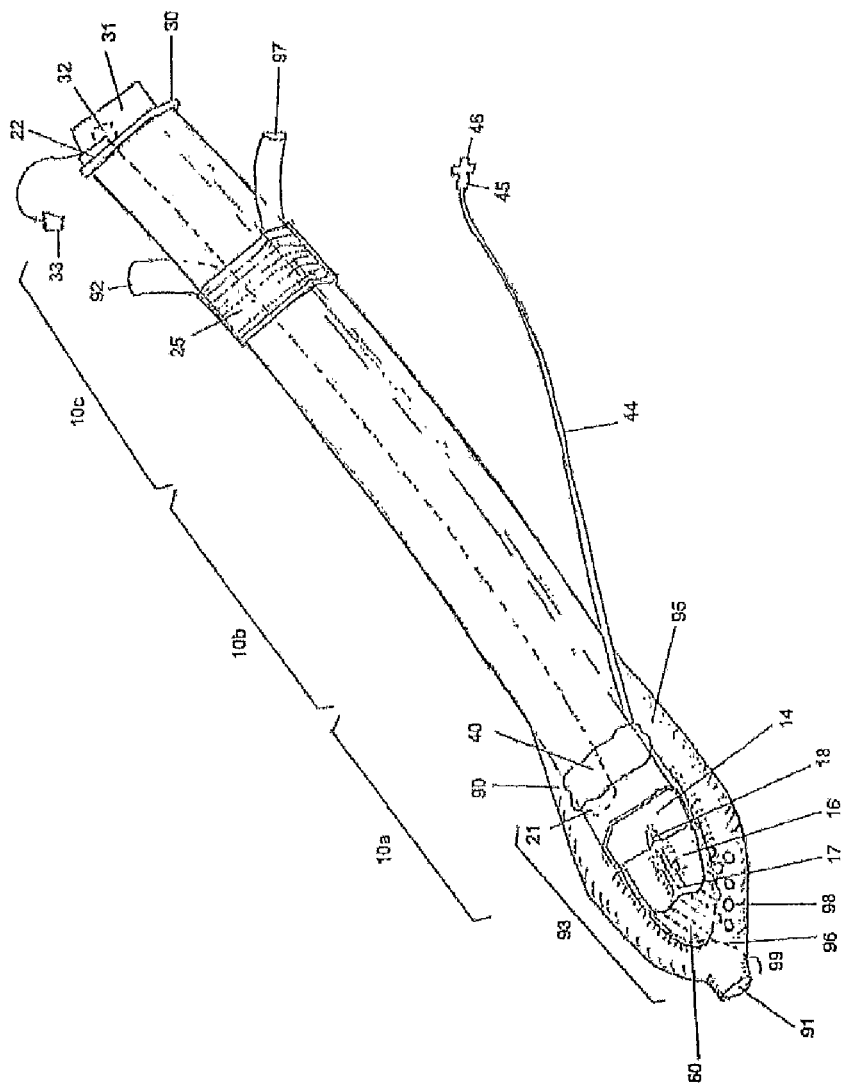
FIG. 1a—Oblique view of ISAD in one embodiment, no restraint plate configuration, with an inflatable balloon deflated, shaded area represent bottom plate.

The present invention is an intubation and supraglottic airway device, brief as ISAD, with various invention embodiments to provide easy and gentle endotracheal intubation, with a choice of "blind intubation". "Blind intubation" means during an intubation an operator does not have to visualize the laryngeal inlet or vocal cord structure directly or indirectly to accomplish the intubation. At present invention operator also can choose to perform the intubation under visualization of a fiber optics scope. The ISAD also can be used as a supraglottic airway device for spontaneous ventilation and positive pressure mechanical ventilation. Further, the ISAD can provide an alternative access for respiratory treatment and laryngology for inspection, removing a foreign body, biopsy and some oral dental surgeries. The present invention can be widely used in multiple medical specialties without waiting a sub-specialty trained physician in emergency difficulty airway cases and be used as an alternative tool for positive pressure mechanical ventilations without an endotracheal tube. And the present invention can also provide an esophageal gastric access for a fiber optic scope probe passing through for diagnosis and treatment procedure of gastric intestinal diseases. Finally, it is also an objective of this invention to be inexpensive to manufacture.

The device may be constructed from any suitable plastics or polymers, or other suitable materials with certain flexibility that allows insertion into a patient's throat without damaging throat tissues.

In one embodiment, the ISAD comprise a tube system with ATAP, an inflatable balloon, and a drainage loop, an esophageal blocker, a bottom plate, a fist drainage tube and a second drainage tube. Preferably the ISAD is configured to add other two components: epiglottis lifting and holding plate, brief as ELHP, and a restraint plate. The tube system is comprised of an air tube that is opened at both proximal end and distal end, and an optional fiber-optic-scope-probe tube that is open on a proximal end and closed on a transparent distal end. The material used to close the fiber-optic-tube-probe tube distal end is preferably transparent and configured to provide substantially distortion free transmission of an image thorough the distal end. The air tube and the fiber-optic-scope-probe tube travel next to each other and can share one or more common wall. The fiber-optic-scope-probe tube is designed to accept any currently available fiber optic scope probe. The fiber-optic-scope-probe will transmit the image to a display screen of a fiber optic scope to let an operator visualize the laryngeal inlet area during intubation. However, this visualization during intubation is not mandatory.

The bottom wall of air tube distal end is configured to have an air tube alignment plate, brief as ATAP, extending out the bottom wall of air tube distal end. The ATAP is configured to be contacted and be restricted during upward movement by posterior wall of the larynx or by a restraint plate. The ATAP is able to align the air tube distal end opening with laryngeal inlet when the device is in an engagement position or near the engagement position and the balloon is inflating. At same time during this alignment control process, the restraint means will create the resistance to the expanded balloon consequently the expanded balloon will compress the lumen of an under balloon segment of a balloon inflation tube to narrow down or near closed status which will generate a great resistance for an operator to stop the balloon inflation at optimal maximum inflation volume. The distance of upward movement of the ATAP and the air tube distal end, and the optimum maximum inflation volume can be variable to accommodate each specific patient's laryngeal anatomy. This process establishes an individually inflation optimizing mechanism to limit over inflation of the balloon.

In a preferred embodiment, top wall of the air tube distal segment is configured to have an epiglottis lifting and holding plate, brief as ELHP. The ELHP obliquely rests inside the lumen of the tube system distal segment. Its tip could be curved and extend outside the lumen of the air tube distal end. The ELHP is designed to be lifted by an incoming stylet or an endotracheal tube. The ELHP can be hold in the elevated position by one or two pairs of lateral support means and consequently the ELHP can keep the epiglottis being elevated position for ventilation, especially for positive pressure mechanical ventilation.

At the proximal end opening of the tube system, the air tube can have a connection interface configured at proximal end of the tube system. The connection interface include an opening configured to be connected with standard 15 mm respiratory equipment and treatment devices without air leakage, a fiber optic scope probe tube opening, and suction/oxygen port. The suction/oxygen port is an opening that can be used alternatively to put in a suction catheter to suction out secretion around the laryngeal inlet area, vocal cords, even down to the tracheal or connect to an oxygen supply source for supplementary oxygen.

An inflatable balloon is configured to wrap around the a length of the tube system distal segment configured to push up the tube system distal segment and ATAP for an alignment control process, and to push the surrounding tissues away to expose the laryngeal inlet when the device is in an engagement position or near the engagement position and an inflatable balloon is inflated thorough an inflation tube. At same time the inflatable balloon forms a seal with surrounding tissue to prevent air leakage. The inflated balloon can also hold the air tube distal end opening in front of the laryngeal inlet.

First drainage tube and second drainage tube extend distally to become the right and left convex segment. The both convex segments constitute the drainage loop. The distal portion of the drainage loop and bottom plate extends distally beyond the air tube distal end. At center of the distal edge of the drainage loop is configured to have an esophageal blocker to block upper esophagus opening. The distal portions of both convex segments are configured to create seals with surrounding tissue in subglottic area. The esophageal blocker is configured to further reinforce the seal at upper esophagus. The bottom plate is coupled and positioned between the right and left convex segment of the drainage loop, together forming a structure like plastic floating "boat". The bottom plate forms the bottom of the "boat". The air tube distal end and the ATAP will be sitting inside the "boat" when the balloon is deflated.

At the distal end esophageal blocker has an opening which is continuation of the distal orifice of the first drainage tube to drain fluid or small particles from upper esophagus. The second drainage tube distal end is closed and attaches to the side wall of distal end of the first drainage tube to form the drainage loop. At distal portion of the convex segment of the second drainage tube, the multiple penetrating holes in the wall are configured to drain the fluid or secretions accumulated in the subglottic area and vent out the escaped air to prevent the stomach insufflation when positive pressure in ventilation is excessively high.

At a preferred embodiment, a restraint plate has been configured and is firmly coupled to the bottom plate or to the drainage loop, or combination of the bottom. The restraint plate upward ramp is configured to be encountered by posterior edge of the laryngeal inlet to generate a resistance to stop advancing ISAD during the device inserting into patient's throat. The ATAP is configured to contact with restraint plate downward ramp first and then the restraint plate distal segment. The restraint plate restricts the upward movement of the ATAP and finally stops the ATAP raising. Consequently the ATAP will align the air tube distal end opening with laryngeal inlet.

And also the close contact between the restraint plate and the ATAP can help to provide a barrier to prevent regurgitated fluid accumulated in subglottic area getting into the laryngeal inlet.

As will be realized, the invention is capable of other and different embodiment and its several details are capable of modification in various respects, all without departing form the invention. Accordingly, the drawing and description are to be regarded as illustration to nature and not in a restrictive or limitation sense. And flowing description will primarily focus on preferred embodiments.

DETAILED DESCRIPTION OF THE INVENTION

The following description of the invention is provided as an enabling teaching of the invention. Those skilled in the relevant art will recognize that many changes can be made to the embodiment described, while still attaining the beneficial results of the present invention. It will also be apparent that some of the desired benefits of the present invention can be attained by selecting some of the features of the present invention without utilizing other features. Accordingly, those skilled in the art will recognize that many modifications and adaptations to the present invention are possible and can even be desirable in certain circumstances. These components can be modified in different configurations and combinations, and re-arrangement of the basic components, or omission of some embodiments of this invention, or these components can be made of different type of materials. However they are still within the scope of this invention. Thus, the following description is provided as illustrative of the principles of the present invention and not a limitation thereof.

For purpose of the drawing and description, the use the word of "proximal" refers to the end of an ISAD closest to the operator when an operator holds the ISAD and is ready to insert the device into a patient's mouth. The reference to the term "distal" refers to the ISAD's end that first enters into a patient's mouth. The term "patient" refers to any person or animal requiring the use of the device. The use of word "posterior" refers to a back side of a patient or animal. The word "anterior" refers to the front side of a patient or toward the epiglottis. Further, the use of the term "communication" is used to mean a path for air, gas, or fluid to flow. For purpose of easy describing, in following the specification, if not otherwise specified, the device is assumed in horizontal position with the tube system on top of the bottom plate. Therefore when the tube system distal segment is moved by an inflated balloon, it will be described as "moving up, rising, or push up, or height of the air tube distal end" and so on. And if the device is described as already inserted into a patient's throat, it will be assumed that patient or animal is in supine position until specified otherwise.

The ISAD can be sized to accommodate different gender and age group of human and selected groups of animals. All components of ISAD can be made with biocompatible materials. These include but are not limited to plastics, polymers, rubbers, metals, a combination thereof, or a combination with other types of materials.

Tube System

The tube system, FIGS. 1a, 2, 3a, 4, 5, 11, in one embodiment comprises an air tube 11, or also interchangeably called air tube lumen 11, an optional fiber-optic-scope-probe tube 20, also called fiber-optic-scope-probe tube lumen 20, a connection interface 30, an air tube alignment plate 16 coupled to the air tube distal end 14. The air tube lumen 11 and fiber optic scope probe tube lumen 20 do not communicate with each other along the tube's length. Thus, a fiber optic scope probe will not be contaminated after each use which reduces the work of cleaning and wear and damage while cleaning and sterilizing the expensive fiber-optic scope. Both the air tube 11 and fiber-optic probe tube 20 are preferably positioned adjacent and parallel to each other along the tube system's longitudinal axis and can share a common wall 19. The proximal end of the fiber-optic-scope-probe tube would keep open and is able to accommodate currently available fiber optic scope probe.

For the purpose of describing the tube system 10, the tube system can be subjectively divided into a proximal segment 10c, a middle segment 10b and a distal segment 10a. The tube system can be formed from different types of materials that are preferably transparent and provides operator visualization through the walls of tube system.

The length of the tube system 10 and diameter of lumens of the tube system can be sized for different age and gender group humans or types of animals. The tube system is of sufficient length to extend from the laryngeal opening to beyond the lips of a human or animal. The tube system can be configured with a bite guard 25 at the proximal segment 10c of the tube system that is sufficiently rigid to prevent a patient or an animal from cutting off or excessively restricting lumens of the tube system. The bite guard 25 can be made of relative rigid plastic materials. The bite guard 25 wraps around a length of the tube system proximal segment 10c and a first drainage tube 90 and a second drainage tube 95 and binds them together without sharp corners. At the top wall or side wall of the tube system, multiple depth marks will be shown.

Each tube within the assembled or formed tube system preferably provides a smooth channel for any instrument or other device to pass through. The tubes system is formed out of materials that is preferably non-allergenic, and with other preferred characteristics including but not limited to being relatively flexible, resilient plastic or polymer, or other type of suitable materials, forming smooth surface, and transparent or semi-transparent. One skilled in the art of producing medical devices would be able to select the materials and techniques for manufacturing. Additionally, walls of the tube system should be sufficiently resilient to withstand the compression force that occurs during its' use.

Preferably the distal segment 10a and middle segment 10b of the tube system are more flexible and resilient so that the tubes can be flexed to follow the curvature of the person's or animal's tongue without excessive force during insertion. The proximal portion of the tube system proximal segment 10c will extend outside of a patient's or animal's mouth. In one embodiment, the tube system distal segment 10a can have a preformed slight upward curve.

The air tube is a hollow tube and is opened at the air tube proximal end 31 and at air tube distal end 14, also interchangeably called air tube distal end opening 14. The air tube lumen 11 can carry air, oxygen, medical gases. Further, the air tube lumen can provide a guide for passing through a stylet, an endotracheal tube, a suction catheter or a combination thereof. The air tube lumen 11 can be formed with different internal dimensions and diameter to accommodate different sized endotracheal tubes to freely pass through the air tube lumen. In a preferred embodiment, the air tube lumen is sized to further include space to insert a suction catheter to clean any blood and secretions that may be around or near to the laryngeal inlet, vocal cords area, or even to insert to the tracheal to suction out secretions.

A cross section of the air tube lumen 11 can be configured in different geometric shapes. The air tube cross section can be in a circle, semicircle, ellipse, semi-ellipse, crescent, oval, triangles, squares, rectangles, trapeziums, kite, diamonds, rhombuses, pentagons, or a combination. Preferably, the shape of the air tube lumen 11 is changing over the course and is a combination shape of the two or more of square or rectangle like with rounded corners where it would contact soft tissues of pharynx.

Figure 4:
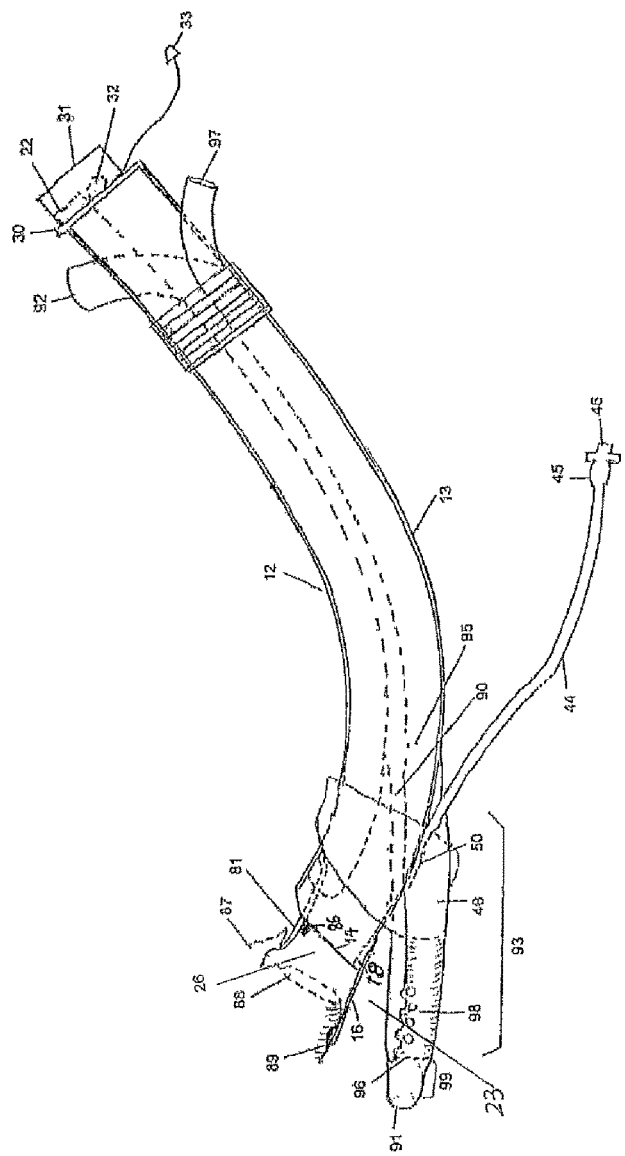
FIG. 4—Left side view of the ISAD in one embodiment, is a side view of the FIG. 3a, when the device inserted and the balloon inflated, the raised ATAP being restricted by posterior wall of the larynx, the ELHP being elevated and held at elevated position by a pair of the lateral support means, the lumen of the under-balloon segment being compressed, the drainage loop slightly tilted to the left for illustrative purpose.

Referring to FIG. 4, 8a, 8b, 9a, 9b1, 11, at the air tube distal end 14, the air tube top wall 12 recedes a short distance. This will form an oblique bevel 15 on right and left side walls of the air tube distal end 14. Therefore, length of top wall 12 of air tube will be shorter than bottom wall 13 of the air tube. The oblique bevel 15 is free of sharp angles or corners and can facilitate a smooth insertion of ISAD into a patient's throat. And the oblique bevel can help to avoid compressing the epiglottis. However, alternatively, the oblique bevel 15 could be omitted.

Preferably the tube system also includes an optional fiber-optic-scope-probe tube 20. The fiber-optic-scope-probe tube is substantially parallel, traveling in same longitudinal direction as the air tube from proximal end to distal end or near distal end in a preferred embodiment, and sharing a common wall 19 with the air tube. The fiber-optic-scope-probe tube 20 can be located at a left or right side of the air tube, in a preferred embodiment at right upper corner of air tube, FIG. 7, 10b, 10c1, 10c2. The fiber optic-probe tube 20 lumen does not communicate with the air tube lumen along the tube lengths. The fiber-optic-scope-probe tube 20 lumen is open at the proximal end 22 and closed at the distal end 21. The fiber-optic tube distal end 21 is closed and formed with a transparent material that transmits light and images substantially undistorted and preferably it has anti-fogging properties. The fiber-optic-scope-probe tube 20 lumen is preferably smaller than the air tube lumen and is configured for commercially available fiber-optic probes to be inserted into the proximal end 22 and advanced down to the distal end 21 for viewing of the laryngeal opening and vocal cord area. The lumen of fiber optic tube 20 will not change during its whole course.

In one embodiment, the distal end of the fiber-optic-scope-probe tube can be configured to be bent downward slightly. Therefore the tip of an inserted fiber-optic probe will be more directly to look at the laryngeal inlet area.

Preferably within no more than 30 mini-meters distance from the oblique bevel 15 of the air tube, the fiber-optic-scope-probe tube 20 is ended distally. From this ending point to the oblique bevel 15, the segment of the shared wall 19 is removed to eliminate any possible distortion of the image from laryngeal area. Therefore at near the air tube distal end 14, the air tube lumen 11 expands to occupy a space which is used to be occupied by the fiber-optic-scope-probe tube. Or in other words, the fiber-optic probe tube distal end 21 terminates inside of the air tube lumen before reaching the oblique bevel 15. Both lumens still don't communicate. Therefore, the cross section area at the air tube distal opening 14 is enlarged and maximized to facilitate ventilation and is larger than other air tube segments' cross section area. Please note, the oblique bevel 15 is a part of the air tube distal end 14.

In an alternative embodiment, the tube system would only have an air tube without a fiber-optic-scope-probe tube. Therefore an operator can insert a fiber-optic-scope-probe through the air tube lumen or can insert a fiber-optic-probe through suction/oxygen port to observe the laryngeal inlet, or do a "blind" intubation without using a fiber optic scope. This configuration of ISAD can still be used as a supraglottic airway device for spontaneous ventilation and mechanical ventilation.

First drainage tube 90 and second drainage tube 95 are firmly attached to the tube system middle segment 10b and portion of the proximal segment 10c on right and left side of the tube system. In a preferred embodiment, the first drainage tube is located at right lower corner of the tube system which is just below the fiber optic scope probe tube, and respectively the second drainage tube is located at the left lower side the tube system, FIGS. 1a, 2, 3a, 5, 10. This right and left arrangement can be switched. The both the drainage tubes may share the common wall with the tube system. In a preferred embodiment, both drainage tubes can occupy or "invade" into a portion of the air tube lumen 11. First drainage tube and the second drainage tube do not communicate with either the air tube lumen 11 or the fiber-optic probe tube lumen 20 along whole length. Both drainage tubes are separated with tube system at the tube system distal segment 10a and become right or left convex segment respectively 93, and extend further beyond the air tube distal end to form a drainage loop. The tube system is positioned between the first and second drainage tubes at the middle segment and a portion of the proximal segment of the tube system. This position arrangement would prevent the tube system distal segment 10a rotation or being twisted and help to stabilize the tube system distal segment in front of the laryngeal inlet after the inflatable balloon inflation.

Alternatively the both drainage tubes can be positioned at the bottom of the tube system.

In an embodiment, a connection interface 30, FIG. 1a, 2, 3a, 4, 5, 10, 11, is configured at proximal end of proximal segment 10c of the tube system. Preferably the connection interface 30 is a continuation of the wall of tube system 10. The connection interface 30 is configured to have a 15 mm standard connector 31 for connecting to a variety of respiratory devices, including a ventilator, an anesthesia circuit, a manual resuscitation bag, a breathing machine, respiratory treatment equipment or a combination thereof. In one embodiment the tube system connection interface 30 has a separate opening near 15 mm standard connector for fiber-optic-scope-probe tube proximal end opening 22 to accept a fiber optic probe. The connection interface 30 also can be configured to have a suction/oxygen port 32, which is next to the 15 mm standard connector. This port would allow either a suction catheter to be inserted into the air tube 11, or allow an oxygen supply tube to be connected to the suction/oxygen port 32 when the suction catheter has been pulled out. The proximal end of the suction catheter would be connected to a suction device to suction out secretions, bleeding or regurgitated gastric content around laryngeal opening area. And after the inserted suction catheter pulled out, an oxygen delivery tube from an outside oxygen source would connect to oxygen port 32 to provide extra oxygen during intubation. There is a removable plug 33 to close the suction/oxygen port. The plug has a connecting wire or string attached to the connection interface 31. After plugging the suction/oxygen port 32 there will be no air leaking from the air tube lumen for spontaneous ventilation and mechanical ventilation. This port 32 could also be used for laryngologist passing through a small surgical instrument for surgery or biopsy. When a suction catheter is inserted into suction/oxygen port 32, the suction catheter is using a spare space after inserting an endotracheal tube into the air tube lumen.

Preferably, at proximal side of the bite guard 25, the first drainage tube and the second drainage tube are separated from the tube system and not connected with the connection interface.

An air tube alignment plate, brief as ATAP has been configured to extend further out beyond the air tithe distal end 14. The ATAP 16 preferably is an extension of the bottom wall or side wall, or combination of both, of the air tube distal end 14, or alternatively the ATAP 16 can be a plate coupled to the air tube distal end 14. The ATAP 16 can be curved as concave or convex shapes, angled or not angled or bifurcated. In shown embodiments, FIG. 1b, 3b, 4, 7, 8a, 9a, 9b, 11, the ATAP 16 is shaped like a trapezoid without sharp angles. Preferably the ATAP 16 is extension and straight plate of the air tube distal end, and preferably is bent up slightly at junction with the bottom wall of the air tube distal end 14. The ATAP 16 can also be other different geometric shapes and their variations, such as: semicircle, ellipse, oval, triangles, rectangle, and so on. However, all those variations and modifications are within the concept and design essence of this invention.

Preferably, the ATAP 16 is configured with a groove like depression along the same longitudinal axis as the tube system, called ATAP groove 17. In one embodiment the ATAP groove 17 is configured to accommodate posterior wall of the larynx. In another embodiment, the shape of the ATAP groove 17 is matched with downward ramp groove 70. However in both configurations, the ATAP groove has same or very similar shape.

Figure 1B:
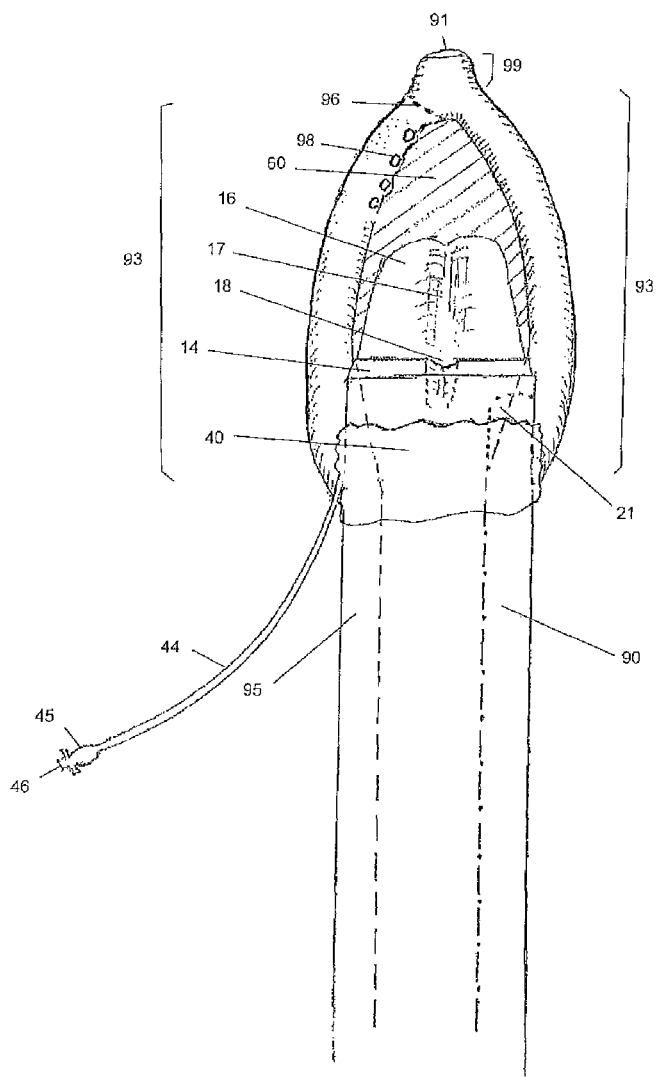
FIG. 1b—Close up detail top view of distal portion of FIG. 1a, the tube system distal segment with ATAP, the drainage loop, the esophageal blocker and the bottom plate, shaded area represent bottom plate.
Figure 8A:
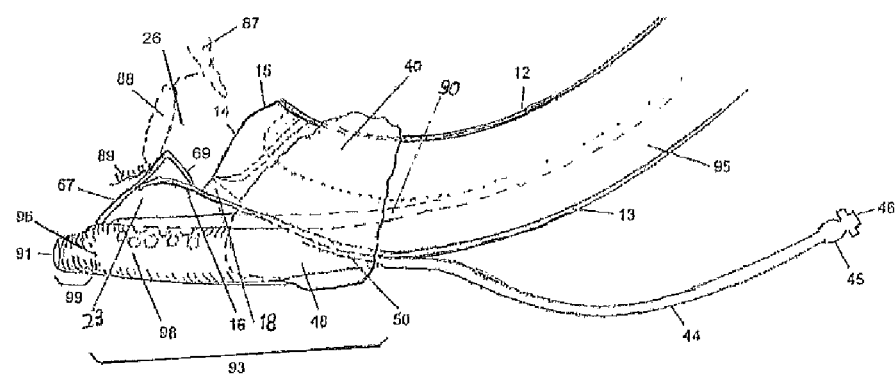
FIG. 8a—Close up detail left side view of the distal portion of the device of FIG. 2, the balloon inflated during the alignment control, ATAP being pushed up and contacting the restraint plate downward ramp and restraint plate distal segment, a pressure buffering chamber and a gas exchange chamber created, the lumen of the under-balloon segment being compressed by the expanded balloon to the near closed status, the drainage loop slightly tilted to the left for illustrative purpose.
Figure 8B:
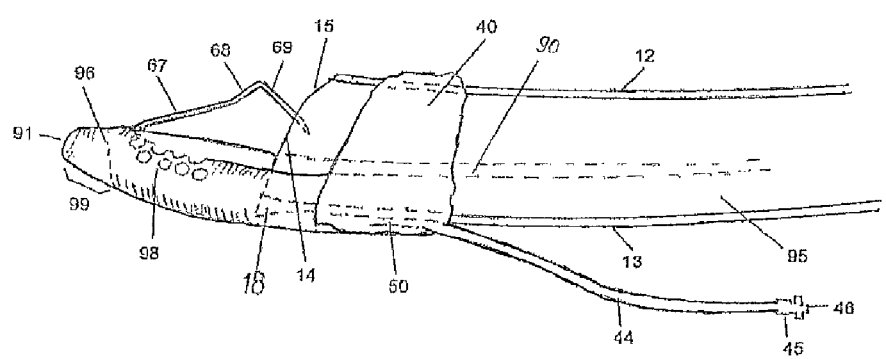
FIG. 8b—Close up left detail side view of distal portion of the device in an alternative embodiment, restraint plate downward ramp elongated and extended into the lumen of air tube distal end opening and not yet contacting the air tube bottom wall groove, no configuration of the ATAP, the balloon deflated and the lumen of the under-balloon segment not being compressed and being open status, the drainage loop slightly tilted to the left for illustrative purpose.
Figure 11:
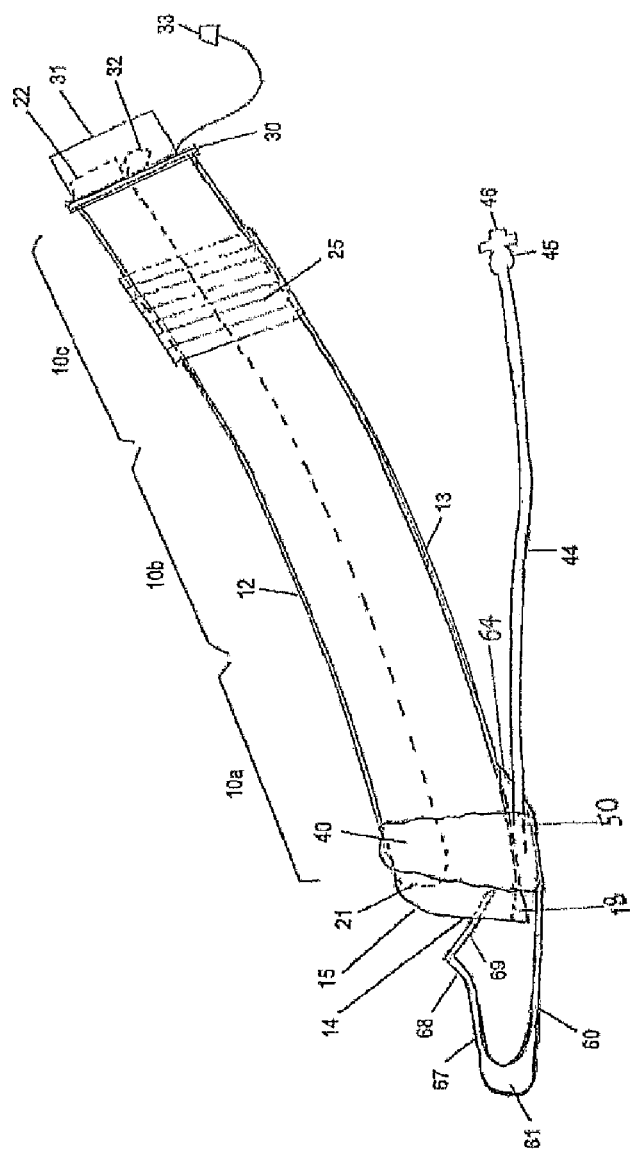
FIG. 11—Left side view of a simplified embodiment, in this configuration, no configuration of the drainage loop, no first drainage tube and second drainage tube, no the ELHP, no the ATAP, the under-balloon segment not being compressed.

In a preferred embodiment, an air tube bottom wall groove 18 is configured at the tube system distal segment 10a, FIG. 1b, 8b11. The air tube bottom wall groove 18 starts at center or near the center of the bottom wall of the air tube distal end 14 and extends proximally a short distance in the same longitudinal axis as air tube. Its shape can be correspondingly matching the downward ramp groove 70 from below to form a conformal contact or a seal. In one embodiment that the ATAP 16 is omitted, FIG. 8b, and restraint plate 65 is configured to extend longer into the lumen of the air tube distal end opening and directly contact with the air tube bottom wall groove 18 when an inflatable balloon inflated. The air tube bottom wall groove 18 also align same longitudinal axis with the ATAP groove 17 and downward ramp 70. Three grooves together can keep the tip of a stylet or endotracheal tube staying in the middle during intubation and guide the stylet or endotracheal tube sliding into laryngeal inlet. Alternatively the each of the three grooves can independently finish same task.

The ATAP is configured to contact a resistance means during the balloon inflation. The resistance means will restrict the height of a raising ATAP 16 and create an increasing resistance and finally a stopping force to stop the upward movement of the ATAP 16 and the air tube distal end as the balloon is inflated more. The resistance means will stop the ATAP 16 raising in front of the laryngeal inlet 88 during the balloon inflation. The resistance means can either be posterior wall 89 of larynx in one embodiment FIG. 4, or a build-in restraint plate in another embodiment, FIG. 2, 8a, 9a.

Preferably the ATAP is made of a type of material with certain flexibility but strong enough to sustain certain depression force.

In one embodiment, an epiglottis lifting and holding plate, brief as ELHP 81, is configured at the top wall of the tube system distal segment 10a. The top wall of the tube system distal segment is cut and divided into three lanes longitudinally by two cutting lines 80, one in left and one in right symmetrically, starting from the distal edge of the top wall of the tube system distal segment toward proximal direction and ending shortly after passing the distal end of the fiber-optic-scope-probe tube 21. The middle lane between the two cutting lines is the ELHP 81. The ELHP 81 splits with right and left lane of the top wall and bends down toward to the bottom wall of the air tube distal end. After the ELHP separates and bends down, the ELHP 81 is configured to become a slender and extend further until its' tip reaches or almost reaches the bottom wall of the air tube distal end. Before the ELHP 81 is elevated, the ELHP 81 is positioned obliquely inside lumen of the air tube. The ELHP's tip is preferably configured to be in slightly curved-up and the ELHP's tip can be inside or outside the lumen of the air tube distal end 14 during its naturally relax position.

The ELHP 81 is a plate and preferably is made same materials as top wall of the tube system distal segment, and preferably is a part of the top wall. But it could be a structure coupled to the top wall of the air tube distal end. Preferably the ELHP 81 is made of materials with elasticity and plasticity, and may be constructed to be thinner than the top wall of the air tube distal end which can give more flexibility. The ELHP 81 can be configured as many different shapes, preferably like a narrow strip with tapered distal end without sharp corners. The ELHP 81 can be configured in other shapes, such as, ellipse, rectangle or triangle, or irregular shapes. All the shapes are configured in a way not to obstruct the ventilation of the air tube when used a supraglottic airway device and not to obstruct the view of the distal end of fiber optic scope probe during operation. The ELHP 81 is configured to have a pair of lateral projection symmetrically branching out from right and left side of the ELHP body at near middle or upper portion of the ELHP 81, called lateral projection 85. The lateral projections 85 extend out form the ELHP body toward right and left side wall of the air tube. At a corresponding location on the left and right wall or edge of the right or left side walls of the air tube distal end 14, a pair of protrusion, bump, or hock is protruding toward to air tube lumen called lateral support means 86. The lateral support means 86 are configured to contact and support the lateral projection 85 from below when the ELHP 81 is lifted up. The ELHP 81 is configured to be elevated by a stylet or an endotracheal tube. Showing in FIG. 4, when the ELHP 81 is being lifted, the lateral projections 85 will be lifted up too and will bounce or travel over the lateral support means 86 due to their elasticity and plasticity. And the lateral support means 86 will support the lateral projections 85 at the elevated position from below, the ELHP 81 will not fall back down even after a lifting force has been withdrawn. The upper surface of the ELHP 81 will touch and hold up the epiglottis 87 to expose or "open" the laryngeal inlet 88 for intubation or the spontaneous ventilation and mechanical ventilation if an ISAD used as a supraglottic airway device.

Please note, the ELHP can be a help in an intubation but is not mandatory for intubation, because the curved tip of a stylet can follow the air tube bottom wall groove 18, ATAP groove 17 and the downward ramp groove 70 to slide into the laryngeal inlet without help from the ELHP 81. Then an endotracheal tube can slide over the stylet into the laryngeal inlet and tracheal to finish the intubation. The major purpose of the ELHP 81 being designed is to guide air flow directly in and out of laryngeal inlet 88 during spontaneous ventilation, especially during positive pressure mechanical ventilation when ELHP is held at an elevated position continuously. This is one of important advantages of the present invention over currently used supraglottic airway devices. The direct air flow can create more laminar flow and reduces turbulent flow, therefore reduces airway resistance and effort for breathing which could play an important role during spontaneous ventilation. In case of positive pressure ventilation, the direct air flow requires less inspiratory pressure to achieve same tidal volume, subsequently possibility of air leakage and the air being forced into the stomach are also reduced, therefore less complication and more effective positive pressure ventilation.

Alternatively, there can have more than one pair of the lateral projections and lateral support means to keep the ELHP 81 at different heights to elevate epiglottis to different height levels.

Alternatively the function of the lateral support means 86 can be performed by hooks, notches, barbs and grooves and so on. In a further alternative embodiment, the lateral support means can be omitted, and the ELHP 81 can be configured to have longer right and left lateral projections 85 folded inside of the air tube lumen before being pushed out and become straight by their elastic property after being elevated and pushed out of the air tube distal end. Consequently, the left and right side edge of the air tube distal end will serve as lateral support means to support the lateral projections 85 prevent the ELHP 81 failing back into the air tube lumen. All these variations are within the essence of this invention.

Inflatable Balloon

An inflatable balloon 40 is configured to wrap around a length of the tube system distal segment 10*a*, FIGS. 1*a*, 1*b*, 2, 3*a*, 3*b*, 4, 5, 8*a*, 8*b*, 9*a*, 9*b*, 10*c*1, 10*c*2, 11. The inflatable balloon can be configured as a complete circle shaped balloon, like a "donut" to encircle a length of the tube system distal segment 10*a* with one inflation tube. However preferably, the lower portion of the balloon which is a portion below the tube system distal segment can be configured to extend a little longer length toward distal and proximal direction along the bottom wall of the tube system, and to have larger lumen for more inflation volume. If from left or right side viewing the device with the balloon inflated, the balloon looks like a "trapezoid" shaped without sharp angles in which the air tube distal end 14 passes through upper portion of the "trapezoid" inflated balloon. The inflated balloon is configured to not obstruct the air tube distal end opening. An inflatable balloon can include internal structure to control the shape of the inflated balloon. After inflation, balloon should be soft and compressible. One skilled in the art of manufacturing medical devices would be able to choose suitable material to meet its performance requirements.

The inflated balloon provides multiple functions when inflated. First, the inflatable balloon pushes up the tube system distal segment 10*a*. The air tube distal end 14 and the ATAP 16 will be raised toward to laryngeal inlet. The ATAP 16 will be sequentially contact the resistance means which can be posterior wall of larynx or a restraint plate in different embodiments and align the air tube distal end opening with the laryngeal inlet when the device is in an engagement position or near the engagement position. Second, the inflated balloon system can push soft tissues above laryngeal inlet aside and root of the tongue away to exposure the laryngeal inlet, especially in an obese patient. At same time, the inflated balloon can form seal with surrounding tissues to prevent air leaking out of the patient's mouth during ventilation. Third, the inflatable balloon will hold or stabilize the air tube distal opening in front or near front of the laryngeal inlet even a patient's head changing to different positions, such as changing to a prone position.

Preferably the inflatable balloon 40 is configured to perform those functions. It is one balloon but can be subjectively divided into upper portion of the balloon and the lower portion 48 of the inflatable balloon 40 for easy description. The lower portion 48 of the balloon is sandwiched between the bottom wall of tube system distal segment 10*a* and the proximal portion of bottom plate 60, FIGS. 4, 8*a*, 9*a*, 9*b*2, and 10*c*. The inflated lower portion 48 of the inflatable balloon 40 separates and elevates tube system distal segment 10*a* from bottom plate 60. In a preferred embodiment, the lower portion 48 of the inflatable balloon 40 is so configured to raise the air tube distal end 14 more than proximal portion of the tube system distal segment 10*a*. After inflation, the taller side of lower portion of the inflatable balloon is just beneath the bottom wall 13 near the air tube distal end 14. The lumen of the lower portion of the inflatable balloon 40 is configured to taper to thinner toward proximal direction.

Figure 2:
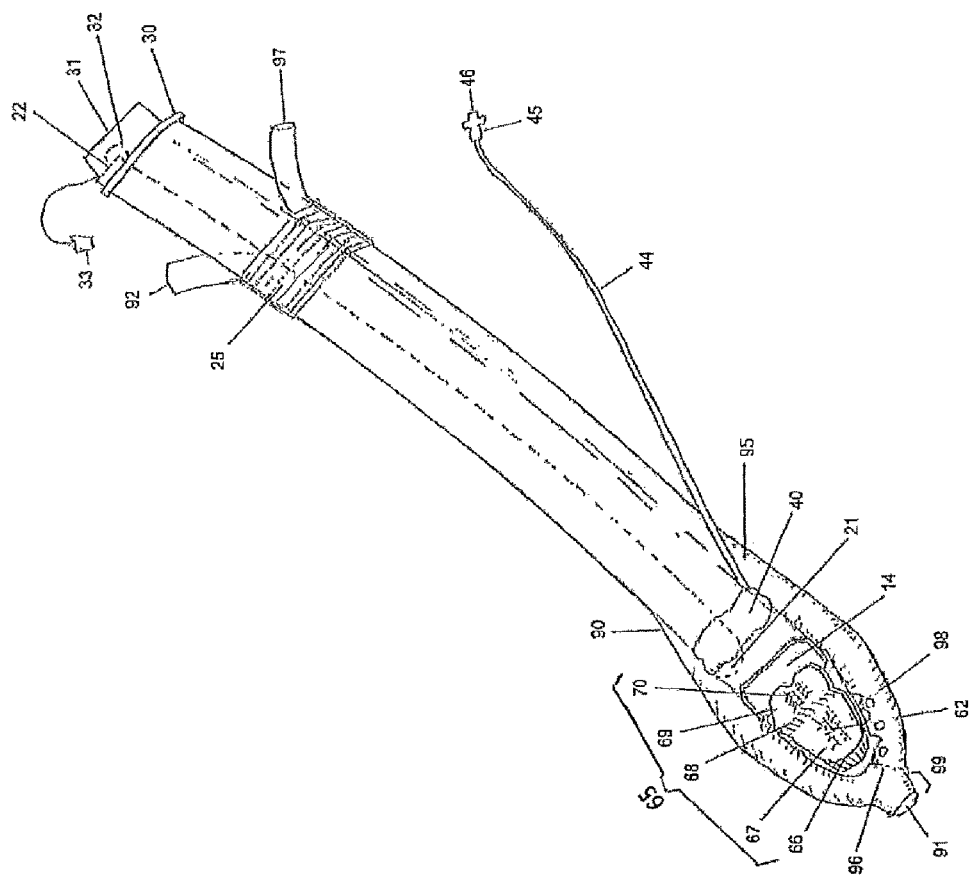
FIG. 2—Oblique view of ISAD, is view of the FIG. 1 with an add-on restraint plate configuration in another embodiment, with an inflatable balloon deflated.
Figure 3A:
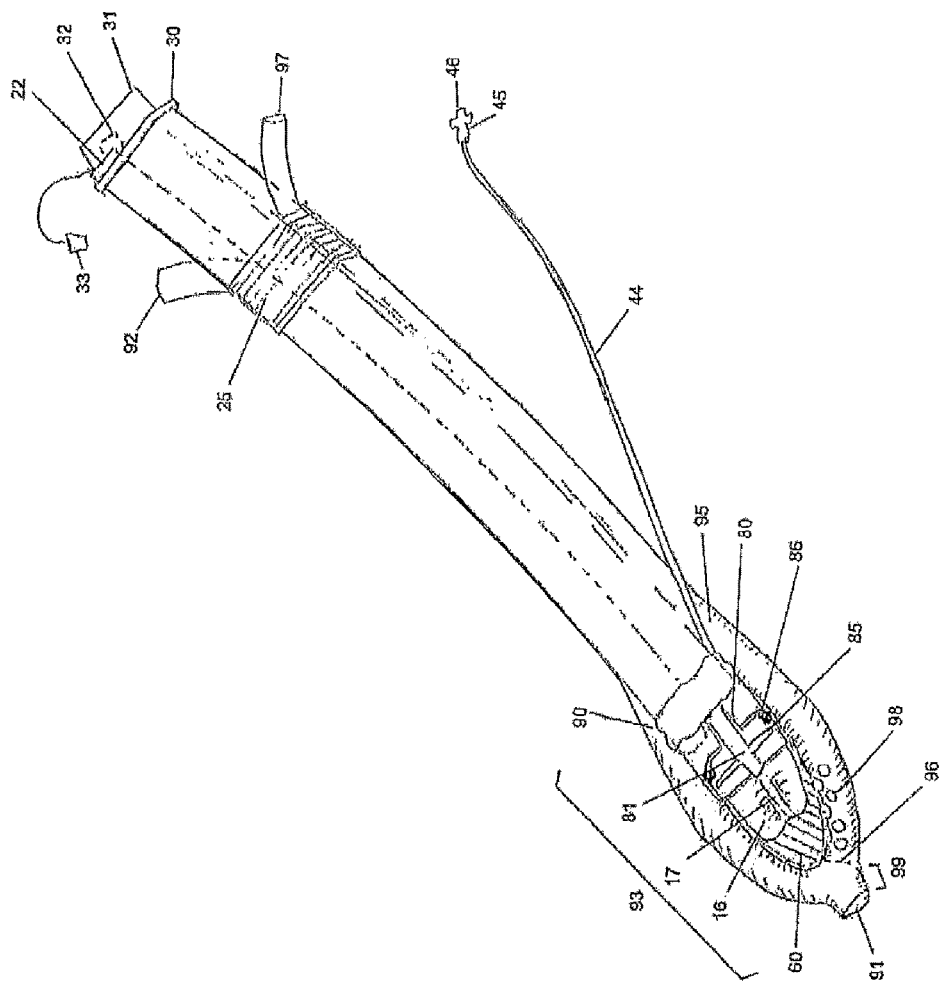
FIG. 3a—Oblique view of ISAD, is view of the FIG. 1 in a preferred embodiment. ELHP has been configured, the ELHP not being elevated, with an inflatable balloon deflated, the restraint plate being removed for illustrative purpose, shaded area represent bottom plate.
Figure 3B:
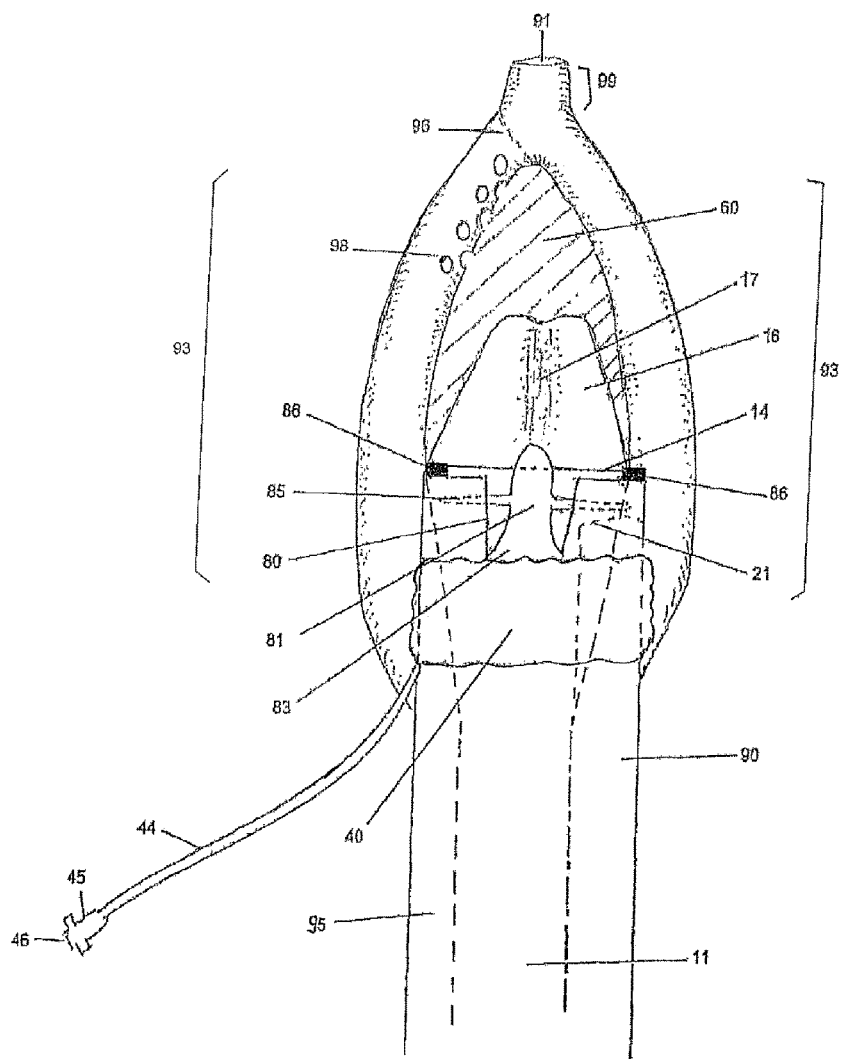
FIG. 3b—Close up detail top view of distal portion of FIG. 3a, the tube system distal segment with the ATAP, the ELHP, the drainage loop, the esophageal blocker, with the balloon deflated, shaded area represent bottom plate.

An alternative embodiment, the configuration of an inflatable balloon can be derived from above described inflatable balloon 40 FIGS. 9*b*1, 9*b*2. An inflatable balloon 43 can be configured to encircle the tube system distal segment 10*a* incompletely from below without top portion of the balloon, or be configured same as the inflatable balloon 40, but the lumen of the top portion of the inflatable balloon 40 which portion is located on top of the tube system distal segment would be occluded. Therefore, the top wall 12 of the tube system distal segment 10*a* or the occluded balloon wall will directly contact the back of the tongue and surrounding tissue to form seal. The lower part of the balloon 43 is configured same shape as the lower portion 48 of the inflatable balloon 40 and would perform same functions as lower portion 48 of the inflatable balloon 40 which is pushing up the tube system distal segment 10*a* and let the air tube alignment plate 16 to align the air tube distal end opening with the laryngeal inlet. Finally this configuration of the inflatable balloon is also able to hold and stabilize the air tube distal end opening in front of the laryngeal inlet.

In a further alternative embodiment, the function performed by the inflatable balloon 40 can be accomplished by two separated inflatable balloons, FIG. 9*a*. One inflatable balloon is like an unclosed cuff band to cover a length of the top, right and left side of the tube system distal segment 10*a*, called top balloon 41. Another inflatable balloon, is configured to couple to the bottom wall of the tube system distal segment 10*a*, called bottom balloon 42. Both balloons 41, 42 do not communicate with each other. The top balloon 41 and the bottom balloons 42 are independent to each other and have their own separate inflation tube to inflate their own lumens. Therefore the operator can control and differentiate the injected volume and pressure in each balloon. In this configuration, preferably the top balloon 41 may have a lower inflation volume or pressure than the bottom balloon 42. Therefore, the top balloon will perform function to push the surrounding tissue away and form seal but exerting less pressure on the mucosa of pharynx to limit possibility tissue damage. On the other hand, the bottom balloon 42 is configured same shape as the lower portion 48 of the inflatable balloon 40 and would perform same function as the lower portion 48 of the inflatable balloon 40 which is pushing up the tube system distal segment 10a and the air tube distal end 14 toward the laryngeal inlet. However, the bottom balloon 42 may require higher pressure than the top balloon 41 to accomplish the task. The two balloons 41, 42 together are also able to hold or stabilize the air tube distal end opening in front of the laryngeal inlet. Further, if an operator decides to use the ISAD as a supraglottic airway device without tracheal intubation, by partially deflating the bottom balloon 42 to decrease the pressure to surrounding tissue and same time to limit air leakage. This maneuver can decrease possibility of tissue damage during a long period of spontaneous or mechanical ventilation. Further by injecting different amount of volume to each balloon independently, an operator may be able to better adjust the height of the air tube distal end related to the laryngeal inlet in certain circumstances. Both balloon 41, 42 can be made by same material or by different types of polymer or plastic materials, preferably with compliant, elastic, expandable and durable natures.

In all above described preferred embodiment or alternative embodiments of the inflatable balloons, each balloon is inflated by an inflation tube 44 through an inflation port 46 with same configuration. A commercially available the pilot balloon 45 is coupled to inflation injection port 46 which could help to estimate the pressure inside of the inflatable balloon FIGS. 4,7, 8a, 8b, 9a, 9b, and 10c, 11

When air, gas, oxygen or liquid are injected into the inflation port, through the lumen of inflation tube, the balloon will be inflated. The inflation injection port 46 is using the commercially available self-sealing valve which can hold injected content without leaking out until an operator purposely withdraw the injected content from the inflation injection port 46 by using a syringe. The inflation injection tube 44 has a small lumen. The inflation tube is very flexible. Its' most course is not to touch other structure and its proximal portion extends out of the patient's mouth.

A short segment of the inflation tube 44 is configured to run a course of between the outer wall of tube system distal segment 10a and the inflatable balloon before penetrating into and communicating with lumen of an inflatable balloon, called-under balloon segment 50. Preferably the under-balloon segment 50 is same size and made same materials as rest of the inflation tube with flexibility, compressible and resilient properties. Alternatively, the under balloon segment can have different diameter of the lumen compared with rest of the inflation tube, and can be made of different materials with those desirable properties. Preferably the under-balloon segment 50 is configured to run a course between the bottom wall 13 of the tube system distal segment 10a and an inflatable balloon. Alternatively, it can also run a course between the top wall or side wall of the tube system distal segment and the inflatable balloon, or combination of the both. In a preferred embodiment, the under-balloon segment 50 is configured to travel between the lower portion 48 of the inflatable balloon 40 and bottom wall 13 of the tube system distal segment 10a, FIG. 8a. In one alternative embodiment, FIG. 9a, the under-balloon segment 50 is configured to travel between the bottom balloon 42 and bottom wall 13 of the tube system distal segment 10a. In another alternative the under-balloon segment 50 is configured to travel between the lower portion of the balloon 43 and the bottom wall 13 of the tube system distal segment. In all these embodiments, all under-balloon segment 50 lumen are configured to be compressed to narrower or near-closed by an external pressure, such as an inflated balloon.

Preferably, a syringe is used to inject gas or liquid into and pull the same out, because a syringe can easily measure how much volume is being injected in and how much is being drawn out.

Drainage Loop and Bottom Plate

With above described tube system and an inflatable balloon, both together can perform some basic functions of the device independently as described above. However, the drainage loop and bottom plate would add more functions to the device. The functions of the drainage loop are to prevent regurgitation of gastric contents and pulmonary aspiration. Further in a preferred embodiment, esophageal blocker 99 is configured on the distal edge of the drainage loop and is configured to be inserted into the opening of upper esophagus to further prevent the regurgitation of gastric contents.

Figure 5:
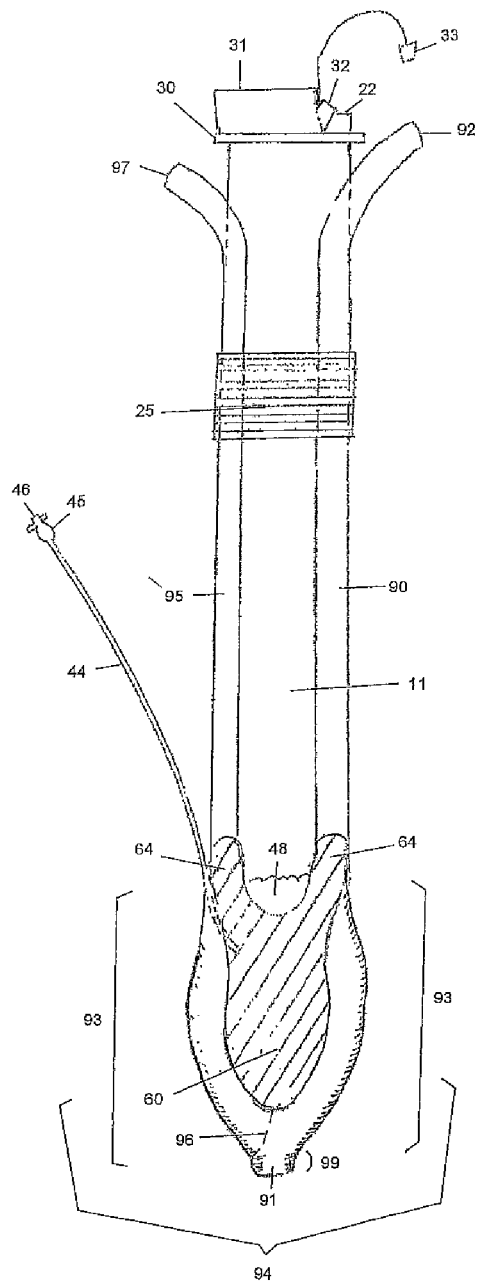
FIG. 5—Bottom view of the ISAD, shaded area represents bottom plate.

The functions of the bottom plate 60 are to strengthen the shape of the drainage loop which makes the drainage loop less easily twisted and to provide the balloon bottom attachment area 63, FIG. 5, 6.

The drainage loop 94 FIG. 5, 6, is constituted by right and left convex segments 93. In a preferred embodiment, the right convex segment 93 is distal extension of the first drainage tube 90, and left convex segment 93 is distal extension of the second drainage tube 95. This right or left position can be switched. The first drainage tube 90 and the second drainage tube 95 are attached to portion of the tube system proximal segment and the entire tube system middle segment, starting at the level of bite guard 25 on the right and left side of the tube system. The first drainage tube and the second drainage tube separate with the tube system distal segment by curving outward away from the tube system distal segment 10a and then curving inward to meet each other and form a loop, called the drainage loop 94. The distal portion of the drainage loop is beyond the air tube distal end 14. Each curved portion of the first drainage tube or the second drainage tube is called convex segment 93. Preferably the cross section area of the convex segment of the first drainage tube is larger than the convex segment of the second drainage tube, FIG. 5, 6, 9b2, 10c. Alternatively, the cross section area of right and left convex segment can be same. But both convex segments curve symmetrically outward and inward in a same horizontal plane to form an ellipse like shaped drainage loop. The convex shape gives more room for the air tube distal opening 14 to expand its lumen. In one embodiment at center of distal edge of the drainage loop is configured to have an esophageal blocker 99. An esophageal blocker 99 is configured to be shaped as a round protrusion, extending further distally from center of the distal edge of the drainage loop in a short distance and taping slightly to a smaller diameter distally. Alternately the esophageal blocker 99 is a reshaped extension of the distal end of the first drainage tube 90. It is a hollow structure with a thicker wall at junction of the esophageal blocker 99 and the drainage loop. This thicker area makes the esophageal blocker 99 less likely to bend or twist. The esophageal blocker 99 is configured like a plug and is to plug and form seal with the upper esophagus opening. Preferably, the esophageal blocker 99 and the drainage loop are made with same material. The esophageal blocker has a distal opening and is a continuation of the first drainage tube distal orifice 91. Therefore, the esophageal blocker 99 also has function to drain the upper esophagus regurgitated contents as well. The first drainage tube 90 lumen and its convex segment, and the esophageal blocker lumen are sized to allow a smaller sized industry standard oral gastric tube passing through into the esophagus and stomach and also configured to accommodate a flexible fiber optic endoscopy probe or a small flexible surgical instrument to pass through to do diagnosis and treatment procedure. Alternatively the esophageal blocker can be omitted, the distal orifice of the first drainage tube would open at the center of the distal edge of the drainage loop to drain the regurgitated fluid in upper esophagus.

The bottom plate 60 is a single flexible plate with certain rigidity. The bottom plate 60 is a flat and smooth plate located between the left and right convex segments of the drainage loop and coupled to the bottom wall or near bottom wall of the convex segments, together forming a structure like a plastic inflatable floating "boat". The bottom plate 60 is a bottom of the "boat". The ATAP and distal portion of the tube system distal segment is setting inside of the "boat" when the inflatable balloon 40 is deflated.

The distal end of the convex segment 93 of second drainage tube 96 is closed and attaches to the distal side wall of the convex segment of the first drainage tube to form the drainage loop 94, FIG. 5,6. The lumens of both convex segments don't communicate. The wall of distal portion of the convex segment 93 of the second drainage tube 95 is configured to have multiple penetrating holes 98 to drain the fluid and small particles accumulated at subglottic area or inside the "boat". And the esophageal blocker and the first drainage tube distal orifice are responsible to drain the fluid or small particles beyond the distal end of the "boat" at upper esophagus opening.

The multiple penetrating holes 98 on the convex segment wall of the second drainage tube are small round holes and their diameter range from 1 mm to 6 mm, total 5-15 holes. The majority of these holes are located on top wall and a side wall facing to another convex segment. The each hole is independent. They serve as communication channels between the subglottic area and the lumen of the convex segment of the second drainage tube. Alternatively, these holes can be other shapes, such as rectangle, square, triangle, ellipse shape and so on.

The convex segments are made of the materials with certain compressibility and plasticity, such as plastics, polymers or other alike. Both can be compressed in a certain extent to accommodate local anatomy to form seal with surrounding tissues. The distal portion of right and left convex segments 93 are configured to form a comfortable seal with surrounding tissues at the subglottic area. The seal, provided by the convex segments 93, can prevent the regurgitated fluid ingress inside the "boat" or subglottic area, and at same time can prevent the ventilating air ingress into the stomach or being pushed into stomach when positive pressure ventilation applied. In addition as described at inflatable balloon section, the inflated inflatable balloons form the seal above the laryngeal inlet. The space between seal created by the inflated inflatable balloon and seal created by the drainage loop is called sealed space. After the ATAP is elevated by the inflated balloon, the ATAP would contact and form a conformal seal with the posterior wall 89 of the larynx or a restraint plate in another embodiment. The right and left side edges of the ATAP will contact the right and left side wall of the pharynx to form contact or seal, and consequently the ATAP separates and divides the sealed space into an upper level, called gas exchange chamber 26, and a lower level, called pressure buffering chamber 23, FIG. 4, 8a, 9a. The gas exchange chamber is like a short channel between the laryngeal inlet and the air tube distal end opening 14 and can guide gas flow in and out of the laryngeal inlet in communication with the air tube distal end opening 14 during ventilation. The top wall and side walls of the gas exchange chamber 26 are patient's pharyngeal anterior wall and side wall tissues. In the preferred embodiment in which the ELHP has been configured, the top wall of the gas exchange chamber would be the epiglottis 87 and ELHP 81 when the ELHP is elevated and hold the epiglottis in an elevated position. And bottom wall of the gas exchange chamber is the ATAP 16 or the ATAP and the restraint plate downward ramp 69 together. Please note, the both chambers 26, 23 are only created or formed after the inflatable balloon inflated and the ATAP is elevated FIG. 4, 8a, 9a, The ATAP may or may not form tight seal with right and left side of the pharyngeal wall. Therefore when applied positive pressure during positive pressure ventilation is higher than usual, the higher pressure may force small portion of the ventilating gas through the contact or seal between the ATAP and right or left side of the pharyngeal wall down into the pressure buffering chamber 23 which is located just below the ATAP. The gas being pushed into the pressure buffering chamber 23 by an excessive positive pressure, called escaped gas. The meaning of the gas here includes air, oxygen and other medical gases. The bottom floor of the pressure buffering chamber 23 is the distal portion of the "boat". After the escaped gas being pushed into the pressure buffering chamber 23, the escaped gas becomes the turbulent flow inside of the pressure buffering chamber until accumulating a certain amount, then the escaped gas passes through the multiple penetrating holes 98 and vents out via the second drainage tube distal orifice 96, instead of being forced to cross the seal created by the drainage loop and the esophageal blocker into esophagus and stomach, or to cross the seal created by the inflatable balloon leaking out patient's mouth. However the escaped gas would be usually minimal or non-exist since an operator can easily control how much positive pressure being delivering by observing a pressure gauge on a breathing machine and adjusting accordingly. As long as the positive pressure delivered is within usually used normal range, the contact or seal between the ATAP's left and right side edge with the laryngeal wall would not allow the ventilating gas being pushed into the pressure buffering chamber. Therefore the multiple penetrating holes 98 only vent out excessively pressured gas when an unusually high positive pressure is applied by an accident or an inexperienced operator.

Because the air tube distal end 14 is just in front of the laryngeal inlet during the device in an engagement position or near the engagement position and the inflatable balloon inflated, the gas exchange chamber can facilitate direct the air flow in and out laryngeal inlet. In addition in a preferred embodiment, the ELHP can hold the epiglottis in open position which can greatly enhance the direct gas flow. In general, the direct gas flow or air flow creates a more laminar flow and reduces turbulent flow. The laminar air flow reduces air resistance and work of breathing which is important when ISAD is used in spontaneous ventilation. Reducing air resistance is especially important in positive pressure mechanical ventilation in which reduced air resistance will significantly decrease the possibility of the air being forced into esophagus and stomach or the air being leaked out, at same time reduced air resistance allows using the higher positive inspiration pressure to achieve more effective ventilation.

These features enable present invention to be used as a supraglottic airway device during positive pressure mechanical ventilation safely and effectively, and are significant in comparison with the prior arts.

Figure 6:
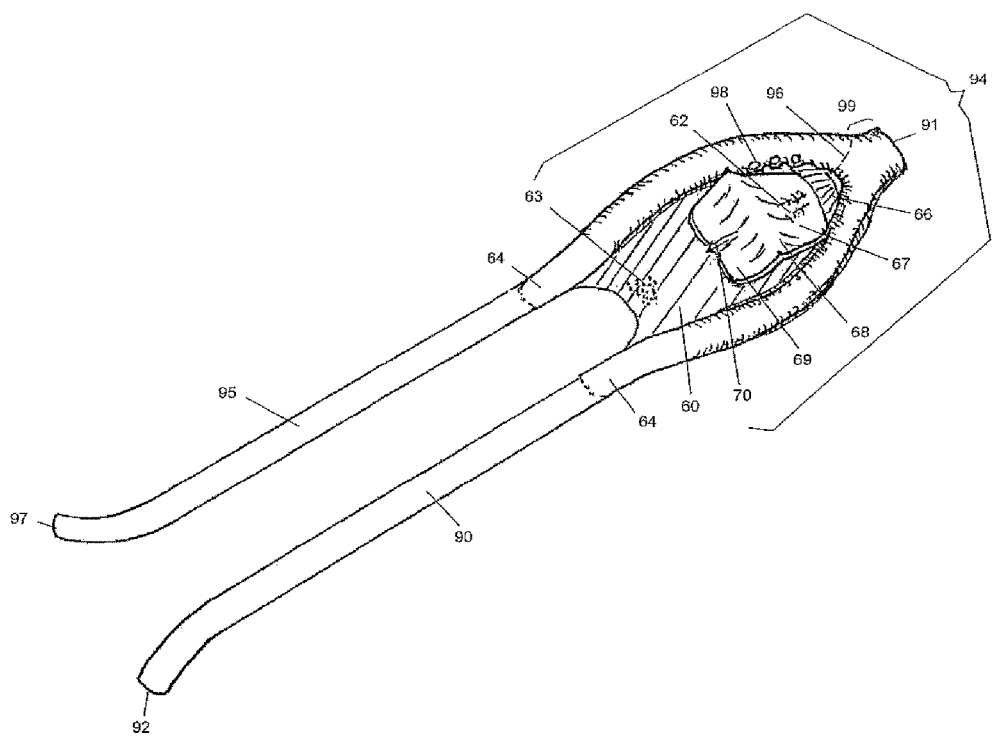
FIG. 6—Oblique view of the drainage loop, esophageal blocker, first drainage tube and second drainage tube, bottom plate, restraint plate, balloon bottom attachment area and bottom plate attachments, shaded area represent bottom plate.
Figure 7:
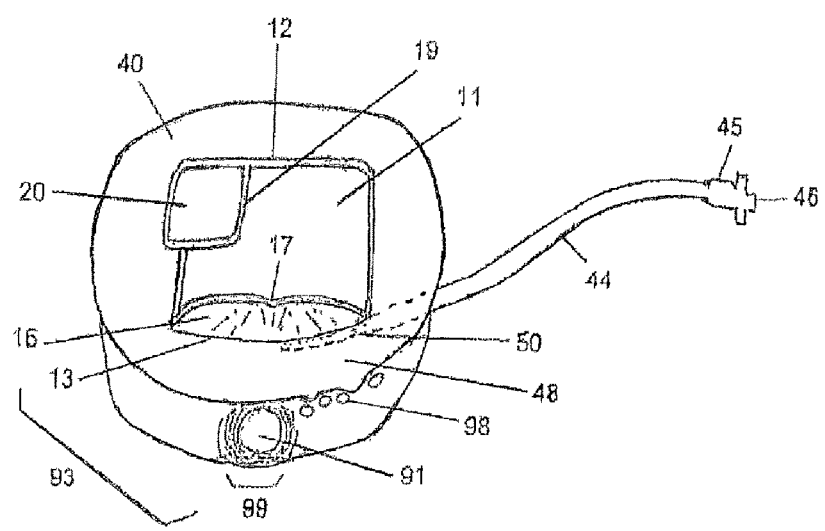
FIG. 7—Close-up detail view of the device from distal end of the device, the balloon inflated and the under-balloon segment being compressed to near closed status, no the ELHP and the restraint plate configuration.

The proximal portion of the bottom plate 60 is just below the inflatable balloon and is preferably coupled to portion of the bottom wall of the balloon in all previous described preferred and alternative embodiments, FIG. 6, 8a, 9a. This area on the bottom plate is called balloon bottom attachment area 63 FIG. 6. The bottom plate does not cover whole bottom wall of the inflatable balloon. Since the inflatable balloon is tightly wrapping around a length of the tube system distal segment and the inflated balloons are compressible, an operator can use the balloon bottom attachment area 63 as an "anchor" or "pivot" area to aim the air tube distal opening 14 to right or left in a horizontal plane in certain extent by operator's hand moving the tube system proximal segment 10c in opposite direction when the inflatable balloon is inflated. Therefor the operator can align the air tube distal end opening 14 with the laryngeal inlet in a horizontal plane. Further, the balloon bottom attachment area 63 can hold the bottom plate 60 and tube system distal segment 10a together in proximity when the inflatable balloon is deflated.

The most proximal side of the bottom plate 60 does not attach to the bottom wall 13 of the tube system. Instead, two narrow plates are configured to branch out symmetrically toward right and left side respectively, both called bottom plate attachment 64. Each bottom plate attachment 64 couples to right or left bottom wall or side wall of the first drainage tube 90 or the second drainage tube 95 respectively. They can extend further to attach to left and right side wall of the tube system FIG. 5. Thereby the bottom plate 60 can be coupled with the tube system distal segment 10a directly or indirectly.

The first drainage tube 90 and the second drainage tube 96 are both hollow tubes for transport of the fluid and small particles and their proximal orifice are to be connected to outside suction devices separately. Cross sections of the first drainage tube 90 and the second drainage tube 95 lumen can be formed in different geometric shapes and their variations, such as: square, rectangle, trapezoid, circle, semicircle, ellipse, semi-ellipse, crescent, oval, triangles, diamonds, or mix or combinations without sharp corners. The shape of the both lumens is changeable throughout the course. In one embodiment, the most of the portion of the both drainage tubes are square shaped without sharp corners at where the corners could contact with surrounding tissues. And the lumen size of the second drainage tube 95 is smaller than the first drainage tube 90, FIG. 10b. Alternatively the lumens size of the both drainage tube can be same. The lumens of the both drainage tubes are smaller than air tube lumen.

In a preferred embodiment, the restraint plate 65 is configured and is preferably made of materials with flexibility and resilient properties. At same time it can stand for certain amount compression force. From most distal to most proximal, the restraint plate can be described as four parts: restraint plate root 66, a restraint plate distal segment 67, an upward ramp 68, and a downward ramp 69. The only restraint plate root 66 is firmly built on the bottom plate 60 or coupled to the wall of the drainage loop, or combination of both by a variety of suitable methods chosen by a specialist. The rest of the restraint plate 65 travels above the bottom plate 60 and is not parallel with the bottom plate 60. This is a space between the two plates, FIG. 6, 8a, 8b, 9a.

And the different portions of the restraint plate or whole restraint plate 65 can be configured as different shaped without sharp angles and corners. They can be shaped like ellipse, oval, triangle, trapezoid, rhombus, square and rectangle and so on.

The restraint plate distal segment 67 is configured to extend toward proximal and upper direction. The restraint plate distal segment has a central depression, groove like area along longitudinal central axis of the restraint plate, called larynx depression 62, FIG. 2,6. The larynx depression 62 is configured to accommodate the anatomic shape of posterior wall of the larynx to form a seal. As restraint plate distal segment extends more toward proximal direction, it bends upward forming a short upward segment, called upward ramp 68. Then the restraint plate bends down forming a downward ramp 69. The upward ramp and downward ramp form an angle below them, called ramp angle. The ramp angle can be changed by lifting up the downward ramp 69, and it will be resume its original angle shape when the lifting force is removed. The downward ramp is final portion of the restraint plate and longer than upward ramp. Alternatively, the upward ramp and downward ramp of the restraint plate can be configured as bow shaped without an angle.

Note, all the above mentioned "couple" or "attach to" between different parts refer to use glue, thermo-adhesive, fasteners or other suitable techniques, or combination thereof or any other suitable technologies.

Alignment Control

In majority of prior arts of supraglottic devices can only use a resistance as stopping point during a device insertion which most likely is due to the tip of device against upper esophagus opening. However the upper esophagus opening is expandable, an inexperienced operator can accidently advance the tip of device too far to have other parts of the device obstructing laryngeal inlet. Second, amount of air need to be injected to inflate a balloon can only be estimated by feeling the firmness of the pilot balloon or its alternatives, or by a manufacture recommended proximal amount. But each patient's anatomy variation and each operator's personal experience to choose difference size of the device to inject different amount of air, make the devices are very difficult to achieve an optimum inflation volume of a balloon for each individual patient to avoid problems caused by over or under inflation. Finally the because of concept and basic shape of the design of prior art of supraglottic airway devises, the air outlet of a device cannot be adjusted to close to the laryngeal inlet. Therefore when the device is used for positive mechanical ventilation, the air leakage is common problem. Thus, the required inspiration pressure for sufficient positive pressure ventilation is hard to achieve.

At present invention, an alignment control concept and related designs are to improve those insufficiencies of the prior arts. First, at present invention, as described at previous section, a restraint plate 65 is configured to have an upward ramp 68 that can create a definitive resistance when the upward ramp 68 encounters the posterior edge of laryngeal inlet during the device insertion. After the device inserting into hypopharynx area, the distal portion of the drainage loop will be entering the space between posterior wall of the pharynx and posterior wall of the larynx and contacting surrounding tissues at subglottic area. And the esophageal blocker will be contacting upper esophagus opening. At this position, an operator's hand which is inserting the device may feel some resistance. However this resistance is not strong enough to stop insertion further. If the operator continues to slightly advance the device, the operator will feel a much stronger resistance and is hard to advance the device more by a commonly used force in clinical practice, because now the restraint plate upward ramp 68 is encountered with the posterior edge of the laryngeal inlet which is creating a definitive resistance to stop advancing the device further. This is an indication for the operator to stop insertion of the device at a proper depth and to avoid inserting too far. This is better position for the air tube distal end ready to be aligned with laryngeal inlet. This indicator may come before the esophageal blocker reach the upper esophagus opening. This is called engagement position of the device. However if the device is just near the engagement position in which the restraint plate upward ramp is within one centimeter distance proximally to the posterior edge of the laryngeal inlet 88 and is called near engagement position of the device, the alignment control elements have been configured and still are able to align the air tube distal end opening with the laryngeal inlet. At this position, the downward ramp will be just adjacent to the laryngeal inlet.

In an alternative configuration, there is no restraint plate configuration 65. During insertion, the air tube distal end 14 or the oblique bevel 15 would encounter laryngeal inlet structures and stop there, FIG. 1*a*, 1*b*, 3*a*, 3*b*. This position also called engagement position in this configuration. Ideally, an operator would pull back the device little to make some space between the air tube distal end and the laryngeal inlet.

The ATAP 16 is configured to contact a restraint means which could be posterior wall of larynx in one embodiment or a restraint plate in another embodiment when the ISAD is in engagement position and an inflatable balloon is inflating. Both restraint means are able to stop ATAP continuously moving upwards in front of the laryngeal inlet and form a tight contact or seal with the ATAP. Therefore the ATAP is able to align the air tube distal end opening with laryngeal inlet at same height for each specific patient (assuming a patient is in a supine position). This is core component of alignment control. Other alignment control related components such as mechanism of optimum maximum inflation volume of the balloon, aiming the air tube distal end 14 in right or left direction, the restraint plate upward ramp 68 stopping at front of laryngeal inlet, will work together to further increase accuracy to align the air tube distal end with laryngeal inlet.

As described before, the restraint plate has four parts. The restraint plate distal segment 67 and downward ramp 69 are designed to contact with the ATAP 16 in a sequential order to create different resistance levels. The restraint plate downward ramp 69 is configured to taper gradually thinner toward the its end suspension edge, therefore the downward ramp 69 can be bent by external force more easily than other parts of the restraint plate. The restraint plate may or may to be configured to extend longer into the air tube distal opening. The downward ramp 69 can be configured as different shapes free of sharp angles and corners, preferably as a trapezoid or rectangle without sharp angles. At same longitudinal direction of the tube system, the downward ramp 69 is configured to have an indentation or depression groove along its central area longitudinally, call downward ramp groove 70. The downward ramp groove 70 is matched the shape of the ATAP groove 17 and the air tube bottom wall groove 18. Therefore ATAP groove 17 can accommodate downward ramp groove 70 comfortably from the below and form a seal. In an alternative embodiment, the downward ramp can extend into the air tube distal end opening 14 and accommodate the shape of the air tube bottom wall groove 18 and form a seal. All three grooves are configured to be able to guide the tip of a stylet or an endotracheal tube into the laryngeal inlet, FIG. 8*a*, 9*a*.

After the ISAD is inserted in an engagement position or near the engagement position before the inflatable balloon 40 inflated, the downward ramp 69 and ATAP 16 is not in contact. When the balloon 40 is being inflated and pushing up air tube distal end 14, the ATAP 16 will be raised too, the upper surface of the ATAP 16 will contact the free suspension edge of the downward ramp first. Because the downward ramp has more flexibility than the ATAP 16 and the ramp angle is changeable, the downward ramp 69 will be lifted up and by the ATAP 16. The free suspension edge of the downward ramp 69 will tightly press against the ATAP 16. And the downward ramp can be bent slightly to have more contact surface area with the ATAP 16. And preferably the most area of downward lamp will contact with the ATAP 16 to form two adjacent layered structure or seal. The seal formed by these two plates can help to prevent fluid and small particles ingress into the laryngeal inlet.

As the inflatable balloon 40 being inflated more and the ATAP 16 being elevated more, the upper surface of distal portion of the ATAP 16 would contact with restraint plate distal segment 67 from below, and stops there, because the restraint plate distal segment 67 is below the posterior wall of the larynx and cannot be pushed up from below. Therefore, the air tube distal end opening 14 now is at same height level of laryngeal inlet and just in front of the laryngeal inlet. In other words, no matter how anterior the laryngeal inlet is located, the ATAP 16 would always bring the air tube distal end to in front of the laryngeal inlet. The ATAP alone or with the downward ramp 69 together function as a "bridge" between the air tube distal end opening and laryngeal inlet for intubation and form the floor of the gas exchange chamber to guide the gas flow in and out of the laryngeal inlet during the ventilation.

In the embodiment without restraint plate configuration, the posterior wall of the larynx would contact with and create a stopping resistance to the rising ATAP 16. The ATAP 16 would align the air tube distal end opening with the laryngeal inlet in similar manner.

In addition the alignment control process can help to establish the optimum maximum inflation volume of the inflatable balloon. The distance between the posterior wall and laryngeal inlet is variable in each patient. As above described alignment control mechanism, the ATAP 16 moving distance from the bottom plate or posterior wall of the pharynx has been individualized by a restraint means in each specific patient. Therefore after the upward movement of the ATAP 16 and the air tube distal end being stopped, the bottom wall 13 of the tube system distal segment will not be pushed up anymore and limit the size of the balloon being further expanded and pressure inside of the inflated balloon will exponentially increase if an operator continues to inflate the balloon. Consequently the inflated balloon will transmit this pressure to compress the lumen of the under-balloon segment 50 to narrow or near closed state. The compressed under balloon segment will exponentially increase the resistance to more inflation. The operator's hand would reliably feel this very quickly greatly increased resistance. The operator would feel that it is hard to further inflate by commonly used usual force in clinical practice, and therefore to stop the balloon inflation at this point. The amount already inflated inside of the inflated balloon is an optimum maximum inflation volume for each specific patient. It can be variable from a subject to another subject and can individually accommodate each individual's laryngeal anatomy variation to avoid over inflation. In other hand if an operator's hand feels minimal resistance which is indication for under inflation, the operator can inflate more.

Therefore, three components: the alignment control, the inflatable balloon and the under-balloon segment 50, together establish a mechanism to achieve the optimum maximum inflation volume, called inflation optimizing mechanism.

This optimum maximum inflation volume would also help to maintain the alignment between the air tube distal end and laryngeal inlet during intubation and ventilation if the ISAD used as a supraglottic airway device.

However, the operator will have ability to manipulate the air tube distal end opening 14 in up and down direction by inflating the inflatable balloon more or less. In addition, as described previously, an operator can aim the air tube distal end opening 14 with the laryngeal inlet in left or right horizontal direction by moving the proximal segment of the tube system in certain extent. These maneuvers can be done with or without under vision of a fiber optic scope. If this is done without vision of the a fiber optic scope, the operator can use currently available intubation stylet, such as but not limited Bougie, which would be inserted into the air tube all the way to the air tube distal end after the ISAD is in engagement position and the balloon is inflated. The depth of the style insertion can be measured by matching the depth mark on the stylet with depth mark on the tube system. The operator's one hand can move the air tube proximal segment 10c slightly in right and left horizontal plan and another hand is advancing the Bougie. The tip of the Bougie will follow the air tube bottom wall groove 18, the ATAP groove 17 and the downward ramp groove 70 toward the laryngeal inlet. Or the operator can rotate the shaft of the Bougie slightly toward right or left to make the tip of the Bougie pointe to right or left "looking for" the laryngeal inlet. Once the Bougie is passing through the laryngeal inlet into the tracheal, the operator's hand which is holding the Bougie will feel sudden loss of the resistance and feel tracheal ring as usual practice. Then the balloon is deflated and the ISAD is withdrawn over the Bougie. And an endotracheal tube is inserted over the Bougie into the tracheal as usual.

At present invention, the name of "restraint plate" built on the bottom plate can have many alternatives and represent a collective restraint means to perform same or similar functions. Here described the restraint plate is just one example of a variety of restraint means. And the functions of the restraint plate 65 and ATAP 16 can be performed by other physically shaped alternatives and interacted each other alternatively, including but not limiting a barb, protrusion, slots, notches, grooves, and indentation, bifurcation, or any other combination of means. But the concept and mechanism of using the restraint means to regulate the moving distance of the air tube distal end opening are essential and within protection scope of this invention.

The restraint plate can be made by a variety of materials, such as not limited, polymers, plastics or even metals.

In an alternative embodiment without configuration of the ATAP, the restraint plate downward ramp 69, FIG. 8b, 11, is configured to extend into the air tube distal opening and to restrict the height of the bottom wall of the air tube distal end and align the air tube distal end opening with the laryngeal inlet during the inflatable balloon inflation when the device is in the engagement position. The downward ramp groove 70 can form a conformal contact and seal with the air tube bottom wall groove 18. The tip of a stylet or an endotracheal tube can be pushed to follow the air tube bottom wall groove 18 and downward ramp groove 70 into the laryngeal inlet, FIG. 2, 7, 11.

A Simplified Embodiment

All previous sections described various embodiments can be perceived as an invention with collection of the preferred and alternative embodiments. Now based on same concepts and design principles, some of parts described above can be omitted and the invention can be simplified for easy and less costly manufacture. For purpose of the easy describing and understanding, it is better to put those changes together as a simplified version of the present invention, FIG. 11, named as a simplified embodiment.

In the simplified embodiment, the all principles and design concepts, described shapes and size of parts and materials made of the parts, position and changing position of the parts or relationship between the parts are same as described above. The methods of use will be same as well. The simplified embodiment is mainly used as a tool for an endotracheal intubation and can be used for a spontaneous ventilation and positive pressure ventilation in selective cases.

Therefore the simplified embodiment will be within same scope of protection of this invention. Claims based on previous described embodiments will be fully applied in this simplified embodiment if same name of the parts have been configured in the simplified embodiment until specified otherwise. Vice versa the claims based on the simplified embodiment configuration are fully applicable to previous described embodiments.

The simplified embodiment FIG. 11, is configured to comprise the tube system, the inflatable balloon 40, the restraint plate 65 and the bottom plate 60. The tube system comprises a same air tube, an optional fiber optic scope probe tube, and a connection interface. But there is no configuration of the ELHP and the ATAP. There is no drainage loop and the first and second drainage tube configuration. The bottom plate 60 has same configuration but bilateral side edge of the bottom plate does not attach to any structures. And the most distal portion of the bottom plate 60 and the root of restraint plate are configured to form an esophageal blocker 61 shaped same as the esophageal blocker 99 built on the drainage loop. But there is no opening at the distal end of the esophageal blocker 61. At most proximal side of the bottom plate 60, the two bottom plate attachments 64 branch out to couple to the side wall of the tube system distal segment 10a. The esophageal blocker 61 of the simplified embodiment is configured to block the upper esophagus opening and prevent aspiration. The inflatable balloon 40 will encircle a length of the tube system distal segment and is configured to work same way as describe previously. The alignment control will be performed by the restraint plate 65. The restraint plate downward ramp 69 will be elongated and extended into the air tube distal end 14 to contact and restrict the upward movement of the bottom wall of the air tube distal end and to align the air tube distal end 14 with the laryngeal inlet and to guide the gas flow in and out the laryngeal inlet. And the downward ramp groove 70 will form a conformal seal with the air tube bottom wall grove 18 to guide the tip of a stylet or an endotracheal tube into the laryngeal inlet. And the restraint plate upward ramp 68 will encounter the posterior edge of the laryngeal inlet and define the engagement position in a same way as described. The balloon inflation tube 44 and the under-balloon segment 50 configuration and working principles are same as the described above. And an optimum maximum inflation volume of the inflatable balloon and the inflation optimizing mechanism will be established same way as described above.

Operational Example

The ISAD can be used as a conduit for an endotracheal intubation, and used as a supraglottic airway device for spontaneous or positive pressure mechanical ventilation. ISAD device is first prepared for insertion. The distal and middle portion of the ISAD are well lubricated, including the tube system middle and distal segment, an inflatable balloon, the bottom plate, the upper surface of restraint plate, the first drainage tube 90, the second drainage tube, and a stylet and outside surface of an endotracheal tube.

Intubation:

The processes can be done utilizing the visualization of a fiber optic scope, or a 'blind" intubation can be performed without using a fiber optic scope. But in both scenario a stylet, such as but not limited Bougie, can be used as a guide.

An operator will use one hand to open a patient's or animal's mouth by using a standard technique. The other hand holds the middle or proximal segment of tube system of ISAD and inserts the distal edge of the drainage loop into the mouth. Once the distal tip is inside of the mouth and against the middle line of the roof of the mouth, the operator can continue to push the ISAD to make the ISAD bend more. Because the tube system is flexible, the middle and distal segment of tube system now is in more curved shape for easily sliding down around the curvature of the back of the tongue. In one embodiment, when the restraint plate distal segment passes behind the posterior wall of larynx and the upward ramp encounter the posterior edge of the laryngeal inlet, an operator's hand will feel a greatly increased resistance and is difficulty to advance more. This is indication that the device is in the engagement position. The depth marks on the tube system's outer wall may be used as reference. In an alternative embodiment without the restraint plate configuration, preferably an operator can pull out the ISAD little before inflating the inflatable balloon.

After ISAD is in the engagement position, an operator will start injecting air, gas or liquid into balloon. An inflatable balloon will raise the air tube distal end opening 14. The ATAP 16 or its alternatives will also be raised up to contact with restraint plate or posterior wall of the larynx in an alternative embodiment. During the balloon inflating, the operator's hand will feel a suddenly increased inflation resistance and can be easily felt by his/her hand, therefore stop further inflation. Now the operator would know that the air tube distal end opening 14 is aligned and facing the laryngeal inlet.

Next, a commercially available stylet with a bent tip, such as, not limited, a Bougie, can be inserted into the air tube lumen with the bent tip facing down. When an operator's hand pushes down the stylet along the air tube, the air tube bottom wall groove, the restraint plate downward ramp groove and ATAP will serves as guide for incoming tip of the stylet. Once the stylet enter the laryngeal inlet and into between vocal cords and tracheal, the operator's hand will feel sudden loss of resistance. This can also be done by utilizing a fiber optic scope. But if an operator chooses not to use fiber optic scope, then the operator can just use feeling the sudden loss of resistance to know the stylet has passed between vocal cords into tracheal. Then an operator will be able to push the stylet further down without resistance and can feel tracheal rings.

In an embodiment with configuration of the ELHP, the tip of an endotracheal tube is able to push up the ELHP and consequently the ELHP lift the epiglottis for the coming endotracheal tube. Therefore the using a style for intubation would be unnecessary.

After the stylet gets into the trachea, the operator's one hand holds the stylet to stay inside the trachea, and the other hand deflate an inflatable balloon and pulls out the ISAD gently along the stylet. Then the distal end opening of an endotracheal tube is put on the proximal end of the stylet and slid down along the stylet into the trachea as usual fashion. Then the stylet is withdrawn. A respiratory device is connected with the endotracheal tube.

Alternatively, an operator may choose to directly use an endotracheal tube passing through the lumen of the air tube into the laryngeal inlet.

And the above the intubation process can be done under the vision of a fiber optic scope, if an operator desires to. Any currently available fiber-optic-scope-probe can be inserted into proximal opening of the fiber-optic-scopo-probe tube on the connection interface and slide all the way to the distal end. The operator can watch the fiber optic scope screen for proper maneuvers.

At a configuration without the fiber-optic-probe-scope-tube, an operator can insert a fiber-optic-probe scope into the suction/oxygen port to view the laryngeal inlet area During the above intubation process, if it takes longer than anticipated or in an obese patient who easily develops oxygen desaturation, an operator can connect a source of oxygen to oxygen/suction port 32 and provide extra oxygen.

And the proximal end opening 92 of the first drainage tube 90 can be connected with a suction device or a proper sized oral gastric tube can be passed through the first drainage tube 90 lumen into esophagus and into stomach to suction out the fluid and small particles.

Finally, a laryngologist can put equipment through a sealable aperture into air tube to reach laryngeal opening area and vocal cords, or down to tracheal, while 15 mm standard connector on the side of the connection interface would connect to breathing machine or other respiratory equipment to ventilate a patient or an animal. This will be another approach for laryngologist to do biopsy or treatment.

Used as a Supraglottic Airway Device:

After ISAD is inserted in an engagement position or near the engagement position as described above, an inflatable balloon can be chosen to inflate to optimal maximum volume as described above. If used for a case of positive pressure mechanical ventilation, after the device is inserted in an engagement position or near the engagement position and the inflatable balloon is inflated, an operator can insert either stylet or an endotracheal tube into the air tube all the way to distal opening, the tip of stylet or the endotracheal tube will raises the ELHP. The raised ELHP will elevate and be kept elevated by the lateral support means. Then the stylet or the endotracheal tube is withdrawn. The elevated ELHP will lift and keep the epiglottis in an elevated position for spontaneous and positive pressure mechanical ventilation. The first and second drainage tube proximal orifice can be suctioned as needed. In a long surgical case, after ISAD is inserted in an engagement position or near the engagement position and inflatable balloon is inflated to the optimum maximum inflation volume, an operator can withdraw some inflated content before hear air leaking. The air leaking can be heard if an operator put his or her ear close to patient or animal's mouth during ventilation. This can further limit pressure on the pharynx tissue and tissue damage.

What is claimed is:

1. An airway device to be inserted in a pharynx comprising:
    a tube system having a tube system distal segment, a tube system middle segment, and a tube system proximal segment, wherein the tube system comprises, an air tube having an air tube distal end opening, and an air tube proximal end opening, and an air tube alignment plate;
    a bottom plate, a restraint plate, and a drainage loop, a first drainage tube and a second drainage tube, wherein the drainage loop comprises a right convex segment and a left convex segment, wherein the right convex segment and left convex segment are extensions of the first drainage tube and the second drainage tube respectively, wherein the first drainage tube and the second drainage tube are attached to a length of right and left sides of the tube system; and an inflatable balloon coupled to a length of the tube system distal segment, and wherein when the device is inserted in an engagement position or near the engagement position and the inflatable balloon is inflated the inflated balloon is configured to move the tube system distal segment away from the bottom plate, wherein the inflatable balloon is configured to move the air tube distal end opening in front of a larynx having a laryngeal inlet when the device is inserted in the engagement position or near the engagement position and push surrounding tissues aside to expose the laryngeal inlet of the larynx, and wherein the inflatable balloon is configured to be connected to and inflated through a lumen of an inflation tube.

2. The device of claim 1, wherein the air tube, having an air tube distal end wall, includes an upper part configured to have a smooth oblique bevel without sharp corners.

3. The device claim 1, wherein the air tube includes an air tube lumen, an air tube length and an air tube cross section, wherein a shape of the air tube cross section varies along the air tube length, wherein the area of the air tube cross section at the air tube distal end is larger than the rest of the air tube lumen.

4. The device of claim 1, wherein the inflatable balloon encircles a length of the tube system distal segment, and when the inflatable balloon inflated, said balloon is configured to hold the air tube distal end opening in front of a laryngeal inlet and form a seal with surrounding tissues, and wherein the inflated balloon stabilizes the tube system distal segment and consequently prevents the drainage loop being twisted.

5. The device of claim 4, wherein the inflatable balloon comprises a portion of the balloon is coupled to the bottom wall of the tube system distal segment, wherein said portion of the balloon is configured to generate a displacement force to raise the tube system distal segment and the air tube alignment plate when the inflatable balloon is inflated, wherein when the inflatable balloon is deflated the deflated balloon will hold the bottom plate and tube system distal segment adjacent with each other.

6. The device of claim 5, wherein the inflatable balloon is configured as a top balloon and a bottom balloon, wherein the top balloon and the bottom balloon are not in communication, wherein both balloons further include their own inflation tube, and wherein each balloon is configured to have different inflation pressures or different inflation volumes.

7. The device of claim 5, wherein the inflatable balloon includes an inflation tube having an inflation-tube lumen, wherein the inflatable balloon is configured to be inflated through the inflation-tube lumen, wherein the inflation tube includes an under-balloon tube segment, wherein the under-balloon tube segment is configured to be compressed narrower or near closed when compressed by the inflatable balloon when inflated.

8. The device of claim 1, further having the air tube alignment plate coupled to the air tube distal end, wherein the restraint plate is configured as a restraint means, wherein the air tube alignment plate is configured to contact with the restraint means and to be restrained and stopped by said restraint means when the device is in the engagement position or near the engagement position and the balloon is inflated, and wherein the air tube alignment plate is configured to be moved up and align the air tube distal end opening with the laryngeal inlet.

9. The airway device of claim 8, wherein the tube system distal segment is configured to be stopped from moving by the restraint means when the device is in the engagement position or near the engagement position and the inflatable balloon is inflating, wherein the stopped tube system distal segment is configured to create an increased resistance to limit the inflated inflatable balloon expansion, wherein the under-balloon segment is configured to be compressed by the inflated inflatable balloon, therein the lumen of the under-balloon segment of the inflation tube is to be compressed to near-closed state, wherein said near closed state of the under-balloon segment generates a greatly increased resistance for an operator to stop the balloon inflation at an optimum maximum inflation volume for each individual subject, thereby an inflation optimizing mechanism is established.

10. The device of claim 8, wherein the air tube alignment plate has an air tube alignment plate groove, wherein said groove is configured to form a seal with the restraint plate, wherein the air tube alignment plate comprises a left side edge and a right side edge, wherein the left and right side edges of the air tube alignment plate will contact or form a seal with a left side wall and a right side wall of the pharynx when the device is inserted in the engagement position or near the engagement position and the inflatable balloon is inflated.

11. The device of claim 10, wherein the air tube alignment plate will contact the posterior wall of the larynx when the device is in the engagement position and the inflatable balloon is inflated and wherein the air tube alignment plate will form a seal with the posterior wall of the larynx.

12. The device of claim 1, wherein the bottom plate further includes a balloon bottom attachment area, wherein the balloon bottom attachment area is configured to couple the bottom plate with the inflatable balloon, wherein said balloon bottom attachment area is configured for the air tube distal end to be able to move toward right or left directions in a certain extent by moving the tube system proximal segment toward left and right directions when said balloon is inflated.

13. The device of claim 1, wherein the first drainage tube and the second drainage tube are configured to bilaterally attach to the tube system middle segment and part of the tube system proximal segment, wherein the first drainage tube and the second drainage tube are configured to stabilize the air tube distal segment after the inflatable balloon is inflated.

14. The device of claim 1, wherein the right and left convex segments of the drainage loop are configured to form a seal with surrounding tissue at a subglottic area and to block the esophageal regurgitation when the device is in the engagement position or near the engagement position, wherein the bottom plate is coupled to the right and left convex segments to strengthen the drainage loop.

15. The device claim of 14 wherein an esophageal blocker is configured at a distal edge of the drainage loop, wherein the esophageal blocker is configured to create a seal with an upper esophageal opening, wherein the esophageal blocker comprises a distal opening to drain regurgitated esophageal gastric contents, wherein the distal opening of the esophageal blocker is a continuation of the first drainage tube distal orifice.

16. The device claim 14, wherein the distal portion of the left convex segment is configured to have multiple penetrating holes, wherein said multiple penetrating holes are configured to drain fluid accumulated in the subglottic area, wherein said multiple penetrating holes are also configured to vent out the excessively pressured gas, wherein a distal end of said convex segment is closed and is coupled to the convex segment of the first drainage tube to form the drainage loop.

17. The device of claim 16, when the air tube alignment plate is configured to form a top of a pressure buffering chamber when the device is in an engagement position or near the engagement position and the inflatable balloon is inflated, wherein the distal portion of the drainage loop and bottom plate are configured to be a bottom of the pressure buffering chamber, wherein the pressure buffering chamber is configured to vent out excessively pressured gas to prevent excessive pressure from pushing the excessively pressured gas into the esophagus or from leaking out the mouth during the positive pressure ventilation.

18. The device of claim 1, wherein the air tube distal end includes a top wall, a right side wall, and a left side wall, and further includes an epiglottis lifting and holding plate coupled to the top wall of the tube system distal segment, wherein the epiglottis lifting and holding plate is configured to be lifted and held in an elevated position continuously, wherein the epiglottis lifting and holding plate is configured to keep the epiglottis at an elevated position continuously when the device is inserted in the engagement position or near the engagement position and when the inflatable balloon is inflated.

19. The device claim 18, wherein the epiglottis lifting and holding plate includes a pair or more of bilateral projections, wherein the lateral projections are configured to extend toward the right side wall and the left side wall, wherein the right and left side walls or right and left edges of the air tube distal end include a pair or more of lateral support means to keep the epiglottis lifting and holding plate at an elevated position after the epiglottis lifting and holding plate is elevated.

20. The device of claim 1, wherein the restraint plate is configured to couple to the bottom plate or the drainage loop, wherein the restraint plate is configured to contact the air tube alignment plate or the bottom wall of the air tube distal end to restrict the upward movement of the air tube distal end when the device is in the engagement position or near the engagement position and when the inflatable balloon is inflated.

21. The device of claim 20, wherein the restraint plate includes a restraint plate distal segment, wherein the restraint plate distal segment further includes a longitudinal depression area to form a seal with the posterior wall of the larynx.

22. The device of claim 21, wherein the restraint plate further includes an upward ramp, wherein the upward ramp is configured to encounter a posterior edge of the laryngeal inlet to create a stopping resistance during device insertion.

23. The device of claim 22, wherein the restraint plate further includes a downward ramp, wherein the downward ramp further includes a downward ramp groove, wherein the air tube alignment plate further includes an air tube alignment plate groove, wherein the downward ramp groove is configured to form a conformal contact and seal with the air tube alignment plate groove, wherein the downward ramp groove is configured to be able to guide a stylet tip and an endotracheal tube into the laryngeal inlet when the device is inserted in the engagement position or near the engagement position and the inflatable balloon is inflated.

24. The device claim 23, wherein said upward ramp and said downward ramp form a ramp angle, wherein the ramp angle is changeable, and wherein the downward ramp is constructed to be bendable.

25. The device claim 1, wherein the tube system distal segment includes an air tube bottom wall groove, wherein the restraint plate is configured to have a downward ramp groove, wherein said air tube bottom wall groove is configured to form seal with the downward ramp groove to guide a stylet tip and an endotracheal tube into the laryngeal inlet when the device is inserted in the engagement position or near the engagement position and the inflatable balloon is inflated.

26. An air way device to be inserted in a pharynx comprising:
a tube system having a tube system distal segment, a tube system middle segment, and a tube system proximal segment, wherein the tube system comprises, an air tube having an air tube distal end opening, an air tube bottom wall grove and an air tube proximal end opening; and
the tube system having a fiber-optic-scope-probe tube, wherein the fiber-optic-scope-probe tube comprises a closed distal end, an open proximal end, and
wherein the closed distal end of the fiber-optic-scope-probe tube runs adjacent to the air tube all the way to near the air tube distal end, wherein the open proximal end of the fiber-optic-scope-probe tube is configured be near the air tube proximal end opening, wherein the closed distal end of the fiber-optic-scope-probe tube end is configured to provide transparent and substantially distortion free transmission of visible light and images; and
a bottom plate having two bottom plate attachments and a balloon bottom attachment area, wherein the bottom plate attachments are coupled to a side wall of the tube system distal segment; and
a restraint plate, wherein the restraint plate is coupled with the bottom plate and forms an esophageal blocker configured to plug an upper esophagus opening and to block regurgitation when the device is in an engagement position, wherein the restraint plate comprises an upward ramp, wherein the upward ramp is configured to contact structures of a laryngeal inlet to stop the device being advanced further, wherein the restraint plate comprises a downward ramp, wherein the restraint plate provides an increasing resistance and finally a stopping force to stop a rising air tube distal end opening in front of the laryngeal inlet, wherein the downward ramp includes a downward ramp groove, wherein the downward ramp groove is configured to form a seal with the air tube bottom wall groove, wherein the downward ramp groove and the air tube bottom wall groove are configured to guide a stylet tip and an endotracheal tube into the laryngeal inlet; and
an inflatable balloon encircling a length of the tube system distal segment, wherein the inflatable balloon is configured to have a lower portion of the inflatable balloon being positioned between the tube system distal segment and the bottom plate, wherein the device is configured that when inserted in the engagement position or near the engagement position and the inflatable balloon is inflated the inflatable balloon moves the tube system distal segment away from the bottom plate and moves the air tube distal end in front of the laryngeal inlet and pushes the surrounding tissues away to expose the laryngeal inlet and forms a seal with surrounding tissues, wherein said lower portion of the inflatable balloon is coupled to said balloon bottom attachment area, wherein the inflatable balloon is configured when deflated to hold the bottom plate and the tube system distal segment in proximity with each other, wherein when the device is in the engagement position or near the engagement position and the inflatable balloon inflated an operator can align the air tube distal end opening with the laryngeal inlet in horizontal plane by moving the tube system proximal segment toward a right or left direction by using said balloon bottom attachment area as pivot point, wherein the inflatable balloon comprises an inflation tube having an inflation tube lumen and is configured to be inflated through the inflation tube lumen and wherein the inflation tube includes a compressible and resilient under-balloon segment, wherein said stopping force provided by said restraint plate increases resistance to the inflated inflatable balloon and consequently the inflated inflatable balloon is configured to compress to the under-balloon segment, therein the inflation tube lumen of the under-balloon segment of the inflation tube is to be compressed to a near-closed state to generate a greatly increased resistance to further inflation, thereby providing an operator an indication to stop inflating the inflatable balloon at an optimal maximum inflation volume for each individual subject, and wherein an inflation optimizing mechanism is established.

27. The device claim 26, wherein the downward ramp extends into the air tube distal end opening and contact and restrict the upward movement of the bottom wall of the air tube distal end and to align the air tube distal end with the laryngeal inlet and form a seal with the bottom wall of the air tube distal end.

* * * * *